US006265473B1

(12) United States Patent
Galbo et al.

(10) Patent No.: US 6,265,473 B1
(45) Date of Patent: Jul. 24, 2001

(54) BLOCK OLIGOMERS CONTAINING 1-HYDROCARBYLOXY-2,2,6,6-TETRAMETHYL-4-PIPERIDYL GROUPS AS STABILIZERS FOR ORGANIC MATERIALS

(75) Inventors: James Peter Galbo, Wingdale, NY (US); Nicola Lelli, Basel (CH); Valerio Borzatta, Bologna (IT); Jean-Pierre Wolf, Courtaman (CH); Michael Ackerman, New City, NY (US); Piero Piccinelli, Sasso Marconi (IT)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 09/424,142

(22) PCT Filed: May 14, 1998

(86) PCT No.: PCT/IB98/00714

§ 371 Date: Nov. 18, 1999

§ 102(e) Date: Nov. 18, 1999

(87) PCT Pub. No.: WO98/54174

PCT Pub. Date: Dec. 3, 1998

(30) Foreign Application Priority Data

May 27, 1997 (EP) .................................. 97810326

(51) Int. Cl.$^7$ ............................ C08K 5/34; C07D 403/14
(52) U.S. Cl. ...................... 524/100; 524/96; 544/198; 544/209; 544/212; 252/403
(58) Field of Search .................... 524/96, 100; 544/198, 544/209, 212; 252/403

(56) References Cited

U.S. PATENT DOCUMENTS 4,086,204 * 4/1978 Cassandrini et al. ............... 260/45.8

(List continued on next page.)

FOREIGN PATENT DOCUMENTS

| 0053775 | * | 6/1982 | (EP) . |
| 0309402 | * | 3/1989 | (EP) . |
| 0357223 | * | 3/1990 | (EP) . |
| 0377324 | * | 7/1990 | (EP) . |
| 0389428 | * | 9/1990 | (EP) . |
| 0435828 | * | 7/1991 | (EP) . |
| 0462069 | * | 12/1991 | (EP) . |
| 0782994 | * | 7/1997 | (EP) . |
| 2301106 | * | 11/1996 | (GB) . |

OTHER PUBLICATIONS

Derwent Abstr. 50507 E/25 for EP 0053775 (1982).*
Chem. Abstr. 97:183468d for EP 0053775 (1982).*

Primary Examiner—Kriellion Sanders
(74) Attorney, Agent, or Firm—Tyler A. Stevenson

(57) ABSTRACT

Compounds of formula (I), in which the polydispersity Mw/Mn is for example 1; n is 2, 3, 4, 5, 6, 7, 8, 9, 10, 11, 12, 13 or 14 the radicals $R_1$ are for example $C_1$–$C_{18}$alkyl or $C_5$–$C_{12}$cycloalkyl; $R_2$ is for example $C_{-C12}$alkylene; the radicals A and B* are independently of one another —$OR_3$, —$N(R_4)(R_5)$ or a group of formula (II); $R_3$, $R_4$ and $R_5$, which are identical or different, are for example hydrogen or $C_1$–$C_{18}$alkyl, or —$N(R_4)(R_5)$ is additionally a group of formula (III) with Y being —O—, —$CH_2$—, —$CH_2$, —$CH_2$— or >N—$CH_3$; X is —O— or >N—$R_6$; $R_6$ is for example hydrogen or $C_{1-C18}$alkyl; R is preferably a group of formula (IV); and B has one of the meanings given for A; with the proviso that in the individual recurrent units of formula (I), each of the radicals B, R, $R_1$ and $R_2$ has the same or a different meaning. The indicated compounds are useful as light stabilizers, heat stabilizers and oxidation stabilizers for organic materials, in particular synthetic polymers.

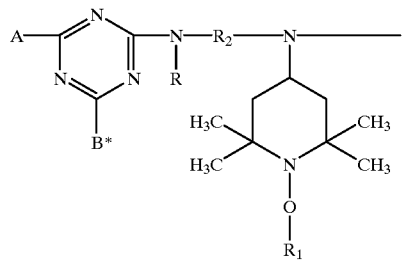

(I)

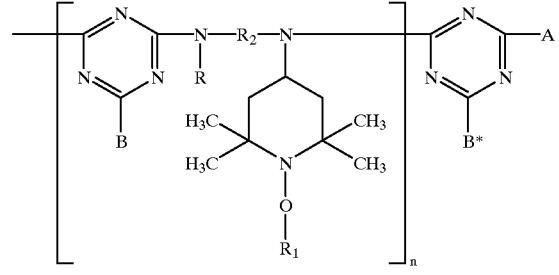

(II)

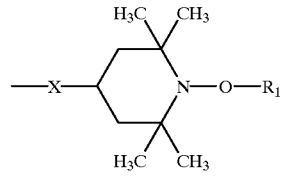

(III)

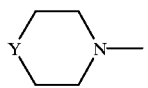

(IV)

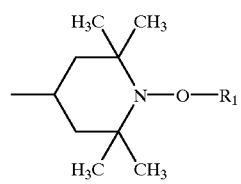

29 Claims, 2 Drawing Sheets

U.S. PATENT DOCUMENTS

Figure 1:
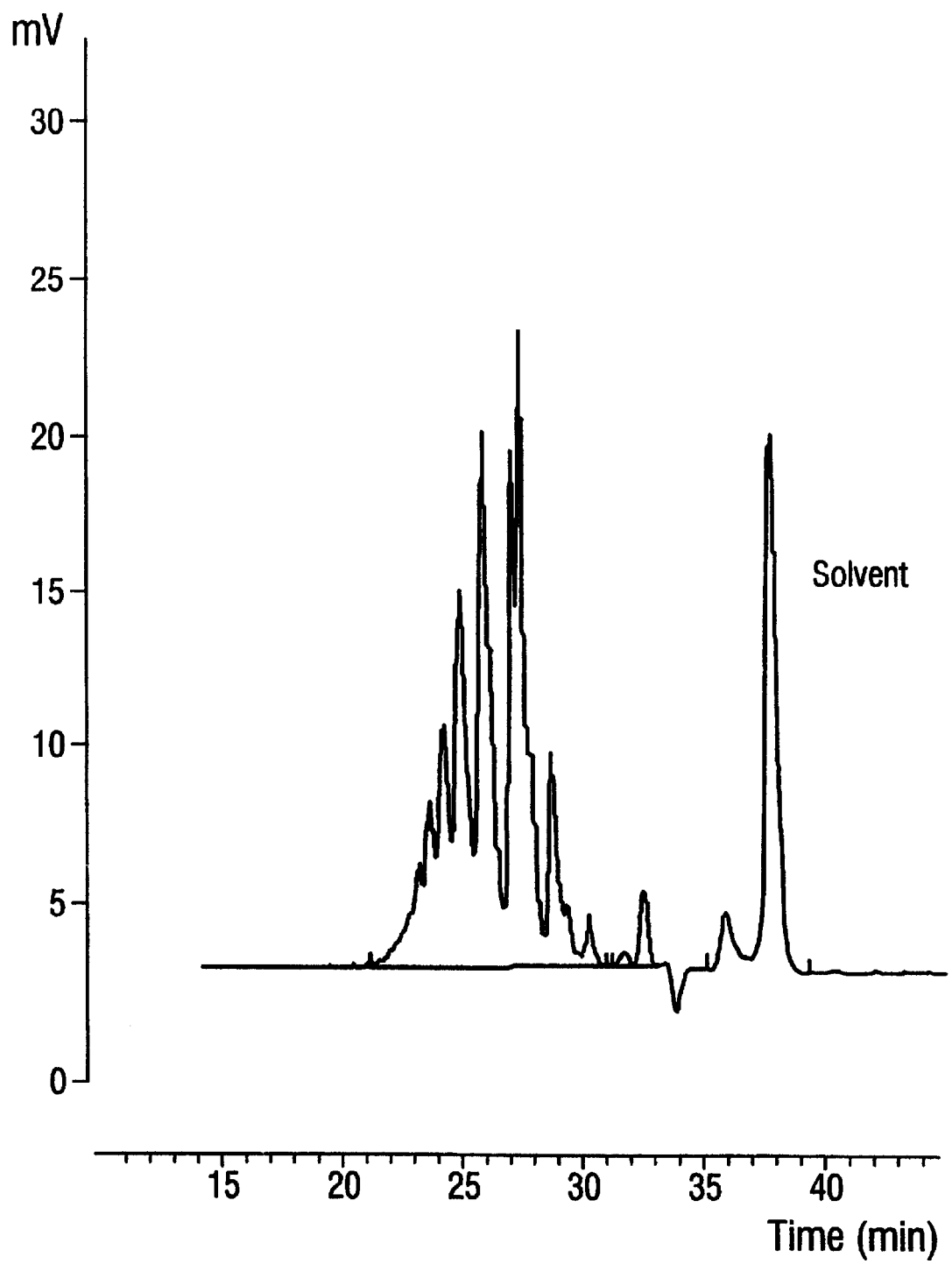

| | | | |
|---|---|---|---|
| 4,234,707 | * | 11/1980 | Rody et al. ............................ 525/437 |
| 4,331,586 | * | 5/1982 | Hardy .................................... 525/186 |
| 4,335,242 | * | 6/1982 | Wiezer et al. ........................ 544/198 |
| 4,459,395 | * | 7/1984 | Cantatore ............................. 524/100 |
| 4,492,791 | * | 1/1985 | Orban et al. ......................... 544/198 |
| 5,004,770 | * | 4/1991 | Cortolano et al. ..................... 524/99 |
| 5,096,950 | * | 3/1992 | Galbo et al. ............................ 524/99 |
| 5,124,378 | * | 6/1992 | Behrens et al. ........................ 524/95 |
| 5,204,473 | * | 4/1993 | Winter et al. ........................ 546/188 |

* cited by examiner

Example V-1
$\overline{M}w/\overline{M}n = 1.53$

BLOCK OLIGOMERS CONTAINING 1-HYDROCARBYLOXY-2,2,6,6-TETRAMETHYL-4-PIPERIDYL GROUPS AS STABILIZERS FOR ORGANIC MATERIALS

The present invention relates to block oligomers containing 1-hydrocarbyloxy-2,2,6,6-tetramethyl-4-piperidyl groups, to their use as light stabilizers, heat stabilizers and oxidation stabilizers for organic materials, particularly synthetic polymers, and to the organic materials thus stabilized. Furthermore, the present invention relates to a mixture with a narrow molecular weight distribution, containing at least three different single block streamers, and to a method of the preparation thereof.

The stabilization of synthetic polymers with derivatives of 2,2,6,6-tetramethylpiperidine has been described for example in U.S. Pat. No. A-4,086,204, U.S. Pat. No. A-4,331,586, U.S. Pat. No. A-4,335,242, U.S. Pat. No. A-4,234,707, U.S. Pat. No. 4,459,395, U.S. Pat. No. A-4 492,791, U.S. Pat. No. 5,204,473, EP-A-53 775, EP-A-357 223, EP-A-377 324, EP-A-462 069, EP-A-782 994 and GB-A-2 301 106.

The present invention relates in particular to a compound of the formula (I)

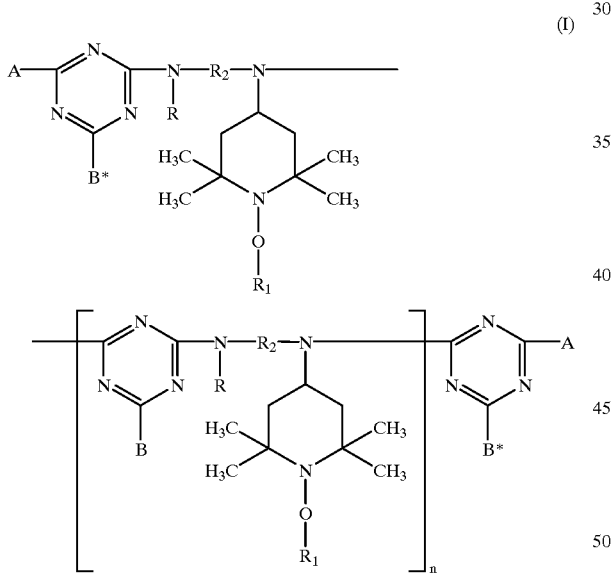

in which n is a number from 2 to 14;

the radicals $R_1$ are independently of one another hydrogen, a hydrocarbyl radical or —$OR_1$, is —O;

the radicals $R_2$ are independently of one another $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N-$X_1$ with $X_1$ being $C_1$–$C_{12}$acyl or ($C_1$–$C_{12}$alkoxy)carbonyl or having one of the definitions of $R_4$ given below except hydrogen; or $R_2$ is a group of the formula (a), (b) or (c);

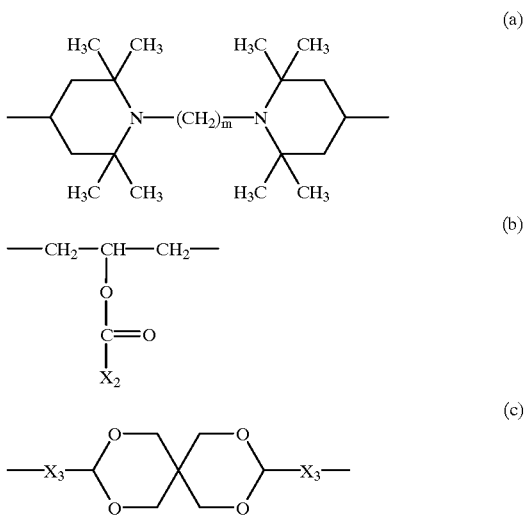

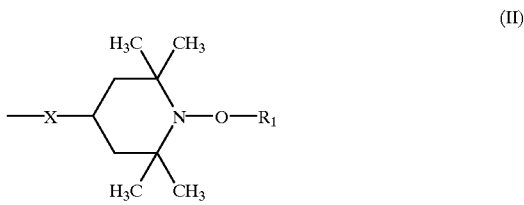

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3$C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

the radicals A are independently of one another —$OR_3$, —$N(R_4)(R_5)$ or a group of the formula (II);

$R_3$, $R_4$ and $R_5$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_1$–$C_2$alky which is substituted in the 2, 3 or 4 position by —OH, $C_1$–$C_8$alkoxy $C_1$–$C_4$alkyl)amino or a group of the formula (III);

(III)

with Y being —O—, —$CH_2$—, —$CH_2CH_2$— or >N—$CH_3$, or —$N(R_4)(R_5)$ is additionally a group of the formula (III)

X is —O— or >N-$R_6$;

$R_6$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV),

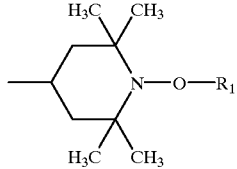

(IV)

or $C_2$–$C_4$alkyl which is substituted in the 2, 3 or 4 position by —OH, $C_1$–$C_8$alkoxy, di($C_1$–$C_4$alkyl)amino or a group of the formula (III);

the radicals R have independently of one another one of the meanings given for $R_6$; and the radicals B and B* have independently of one another one of the meanings given for A;

with the proviso that in the individual recurrent units of the formula (I), each of the radicals B, R, $R_1$ and $R_2$ has the same or a different meaning.

in the individual recurring units of the formula (I), each of the radicals B, R, $R_1$ and $R_2$ has preferably the same meaning, In the formula (I), the radical R and the radical

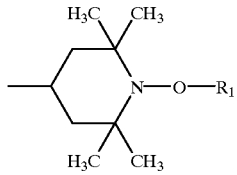

can have a random distribution or a block distribution.

$R_1$ is preferably a hydrocarbyl radical having 1 to 18 carbon atoms.

$R_1$ as a hydrocarbyl radical is for example $C_1$–$C_{18}$alkyl, $C_5$–$C_{18}$alkenyl, $C_5$–$C_{18}$alkynyl, $C_5$–$C_{12}$cycloalkyl unsubstituted or substituted by $C_1$–$C_4$alkyl; $C_{5-C12}$cycloalkenyl unsubstituted or substituted by $C_1$–$C_4$alkyl; a bicyclic or tricyclic hydrocarbyl having 6 to 10 carbon atoms or $C_7$–$C_9$phenylalkyl unsubstituted or substituted on the phenyl by $C_1$–$C_4$alkyl;

Examples of alkyl containing not more than 18 carbon atoms are methyl, ethyl, propyl, isopropyl, butyl, 2-butyl, isobutyl, t-butyl, pentyl, 2pentyl, hexyl, heptyl, octyl, 2-ethylhexyl, t-octyl, nonyl, decyl, undecyl, dodecyl, tridecyl, tetradecyl, hexadecyl and octadecyl. $R_1$ is preferably $C_1$–$C_{12}$alkyl, in particular $C_1$–$C_8$alkyl. $R_4$, $R_5$ and $R_6$ are preferably $C_1$–$C_5$alkyl, in particular $C_1$–$C_4$alkyl.

An example of $C_2$–$C_4$alkyl substituted by —OH is 2-hydroxyethyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl) amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

The group of the formula (III) is preferably

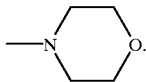

Preferred examples of $C_2$–$C_4$alkyl substituted by a group of the formula (III) are groups of the formula

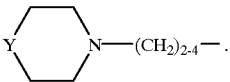

The group

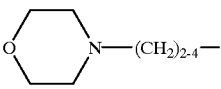

is particularly preferred.

Examples of $C_5$–$C_{12}$cycloalkyl which is unsubstituted or substituted by 1, 2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclodoclecyl. Unsubstituted or substituted cyclohexyl is preferred.

A preferred example of a bicyclic or tricyclic hydrocarbyl radical having 6 to 10 carbon atoms is 1,2,3,4-tetrahydronaphthenyl.

A preferred example of $C_5$–$C_{12}$cycloalkenyl unsubstituted or substituted by $C_1$–$C_4$alkyl is cyclohexenyl.

Examples of alkenyl containing not more than 18 carbon atoms are allyl, 2-methylallyl, butenyl, hexenyl, undecenyl and octadecenyl. Alkenyls in which the carbon atom in the 1-position is saturated are preferred.

A preferred example of $C_5$–$C_{18}$alkynyl is octynyl.

Examples of phenyl substituted by 1, 2 or 3 $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl which is unsubstituted or substituted on the phenyl by 1, 2 or 3 $C_1$–$C_4$alkyl are benzyl, methylbenzyl, dimethylbenzyl, trimethylbenzyl, t-butylbenzyl and 2-phenylethyl. Benzyl is preferred.

Examples of acyl (aliphatic, cycloaliphatic or aromatic) containing not more than 12 carbon atoms are formyl, acetyl, propionyl, butyryl, pentanoyl, hexanoyl, heptanoyl, octanoyl and benzoyl. $C_1$–$C_{18}$Alkanoyl and benzoyl are preferred. Acetyl is especially preferred.

Examples of ($C_1$–$C_2$alkoxy)carbonyl are methoxycarbonyl, ethoxycarbonyl, propoxycarbonyl, butoxycarbonyl, pentoxycarbonyl, hexoxycarbonyl, heptoxycarbonyl, octoxycarbonyl, nonyloxycarbonyl, decyloxycarbonyl, undecyloxycarbonyl and dodecyloxycarbonyl.

Examples of alkylene containing not more than 12 carbon atoms are ethylene, propylene, trimethylene, tetramethylene, pentamethylene, hexamethylene, octamethylene, decamethylene and dodecamethylene. $R_2$ is for example $C_2$–$C_8$alkylene or $C_4$–$C_8$alkylene, in particular $C_2$–$C_6$alkylene, preferably hexamethylene.

An example of $C_4$–$C_{12}$alkenylene is 3-hexenylene.

An example of $C_5$–$C_7$cycloalkylene is cyclohexylene.

Examples of $C_4$–$C_{12}$alkylene interrupted by 1,4-piperazinediyl are

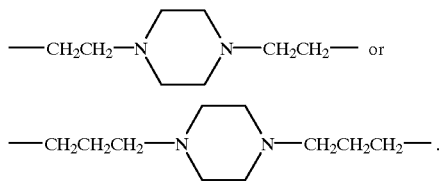

Examples of $C_4$–$C_{12}$alkylene interrupted by —O—, e.g. 1, 2 or 3 —O—, are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

Examples of $C_4$–$C_{12}$alkylene interrupted by >N-$X_1$ are —$CH_2CH_2CH_2$—N($X_1$)—$CH_2CH_2$—N($X_1$)—$CH_2CH_2CH_2$—, in particular —$CH_2CH_2CH_2$—N($CH_3$)—$CH_2CH_2$—N($CH_3$)—$CH_2CH_2CH_2$—.

An example of $C_5$–$C_7$cycloalkylenedi($C_1$–$C_4$alkylene) is cyclohexylenedimethylene.

Examples of $C_1$–$C_4$alkylenedi($C_5$–$C_7$cycloalkylene) are methylenedicyclohexylene and isopropylidenedicyclohexylene.

An example of phenylenedi($C_1$–$C_4$alkylene) is phenylenedimethylene.

The variable n is preferably a number from 2 to 12, in particular 2 to 6.

Those compounds of the formula (I) are preferred, wherein the polydispersity $\overline{M}w/\overline{M}n$ is 1 and n is 2, 3, 4, 5, 6, 7, 8, 9, 10, 11, 12, 13 or 14.

Polydispersity indicates the molecular-weight distribution of a polymeric compound. In the present application, the polydispersity is the ratio of weight-average ($\overline{M}w$) and number-average ($\overline{M}n$) molecular weights. A value of $\overline{M}w/\overline{M}n$ equal to 1 means that the compound is monodispers and has only one molecular weight and no molecular weight distribution. A narrow molecular weight distribution is characterized by a polydispersity $\overline{M}w/\overline{M}n$ close to 1.

When the polydispersity $\overline{M}w/\overline{M}n$ is 1, n is preferably 2, 3, 4, 5, 6, 7, 6, 9, 10, 11 or 12, in particular 2, 3, 4, 5 or 6, for example 2, 4 or 6.

R is preferably hydrogen, $C_1$–$C_{10}$alkyl, cyclohexyl or a group of the formula (IV), in particular hydrogen or a group of the formula (IV). R as a group of the formula a (IV) is especially preferred.

$R_1$ is preferably hydrogen, $C_1$–$C_{12}$alkyl or $C_5$–$C_8$cycloalkyl, in particular $C_1$–$C_8$alkyl or cyclohexyl, for example methyl, octyl or cyclohexyl.

The radicals A and B* are preferably —N($C_1$–$C_4$alkyl)$_2$.

A preferred embodiment of the instant invention relates to a compound of the formula (I) wherein n is a number from 2 to 12;

$R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi($C_1$–$C_4$alkylene);

$R_6$ is hydrogen, $C_1$–$C_{18}$alkyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV) or $C_2$–$C_4$alkyl which is substituted in the 2, 3 or 4 position by —OH, $C_1$–$C_8$alkoxy, di($C_1$–$C_4$alkyl)amino or a group of the formula (III); and R is a group of the formula (IV).

A preferred compound of the formula (I) is that wherein $R_2$ is $C_2$–$C_{10}$alkylene, cyclohexylene, cyclohexylenedi($C_1$–$C_4$alkylene), $C_1$–$C_4$alkylene-dicyclohexylene or phenylenedi($C_1$–$C_4$alkylene);

$R_3$, $R_4$ and $R_5$, which are identical or different, are hydrogen, $C_1$–$C_{12}$alkyl, $C_5$–$C_7$cycloalkyl which is unsubstituted or substituted by 1, 2 or 3 $C_1$–$C_4$alkyl; $C_3$–$C_{12}$alkenyl, phenyl which is unsubstituted or substituted by 1, 2 or 3 $C_1$–$C_4$alkyl; benzyl which is unsubstituted or substituted on the phenyl by $C_1$–$C_4$alkyl; tetrahydrofurfuryl or $C_2$–$C_3$alkyl which is substituted in the 2 or 3 position by —OH, $C_1$–$C_4$alkoxy, di($C_1$–$C_4$alkyl)amino or a group of the formula (III); or —N($R_4$)($R_5$) is additionally a group of the formula (III); and $R_6$ is hydrogen, $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; tetrahydrofurfuryl, a group of the formula (IV) or $C_2$–$C_3$alkyl which is substituted in the 2 or 3 position by —OH, $C_1$–$C_4$alkoxy, di($C_1$–$C_4$alkyl)amino or a group of the formula (III).

A particularly preferred compound of the formula (I) is that wherein $R_2$ is $C_2$–$C_8$alkylene;

$R_3$, $R_4$ and $R_5$, which are identical or different, are hydrogen, $C_1$–$C_8$alkyl, cyclohexyl which is unsubstituted or substituted by methyl; $C_3$–$C_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or —N($R_4$)($R_5$) is additionally 4-morpholinyl; and $R_6$ is hydrogen, $C_1$–$C_8$alkyl, cyclohexyl which is unsubstituted or substituted by methyl;

benzyl, tetrahydrofurfuryl, a group of the formula (IV) or $C_2$–$C_3$alkyl substituted in the 2 or 3 position by —OH, $C_1$–$C_4$alkoxy, dimethylamino, diethylamino or 4-morpholinyl.

A compound of the formula (I) of special interest is that wherein n is a number from 2 to 6;

$R_2$ is $C_2$–$C_6$alkylene;

A is —N($R_4$)($R_5$) or a group of the formula (II);

$R_4$ and $R_5$, which are identical or different, are hydrogen, $C_1$–$C_8$alkyl, 2-hydroxyethyl or 2-methoxyethyl or —N($R_4$)($R_5$) is additionally 4-morpholinyl;

X is >N$R_6$, $R_6$ is $C_1$–$C_4$alkyl; and the radicals B and B* have independently of one another one of the definitions given for A.

A further compound of the formula (I) which is of special interest is that wherein B* is different from B and each of the radicals B, R, $R_1$ and $R_2$ has the same meaning in the individual recurring units of the formula (I).

A further embodiment of this invention is a product of the formula (I) having a polydispersity $\overline{M}w/\overline{M}n$ of 1.1 to 1.7. More specifically, this product corresponds to a mixture containing at least three different monodispers ($\overline{M}w/\overline{M}n=1$) compounds of the formula (I) which vary only by the variable n, said mixture having a polydispersity $\overline{M}w/\overline{M}n$ of 1.1 to 1.7.

A mixture having a polydispersity $\overline{M}w/\overline{M}n$ of 1.1 to 1.6 or 1.2 to 1.6 or 1.25 to 1.6, in particular 1.3 to 1.6 is preferred.

A preferred mixture which has for example a polydispersity of 1.1 to 1.7 contains a monodispers compound of the formula (Ia), a monodispers compound of the formula (Ib) and a monodispers compound of the formula (Ic), said compounds differing only in the number of the repetitive units

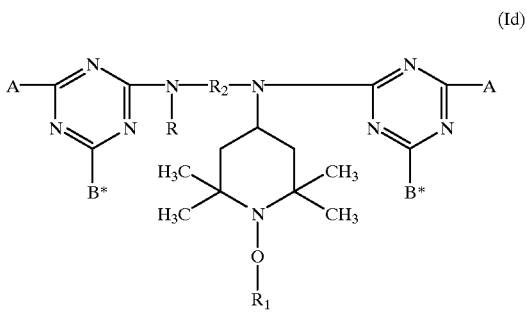

(Id)

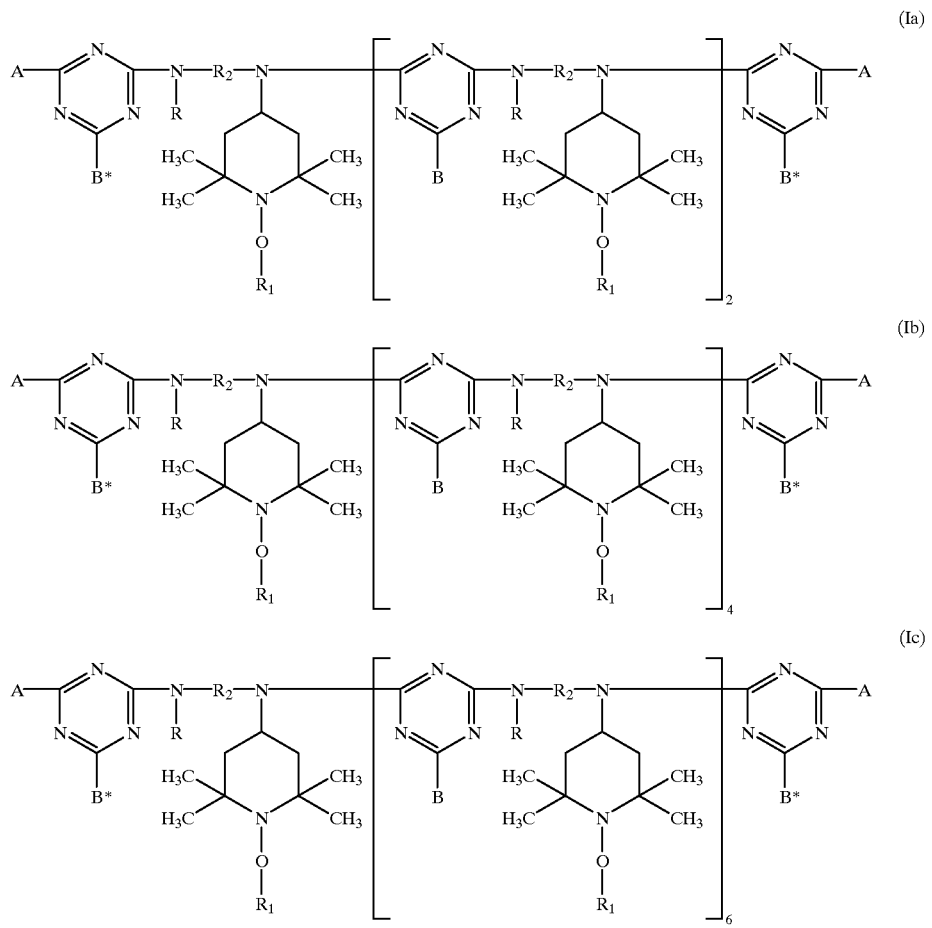

the radicals A, B, B*, R, $R_1$ and $R_2$ are as defined above, and the ratio of the compounds of the formula (Ia) to (Ib) to (Ic) in molar % is preferably 2:1.6:1 to 2:0.5:0.05, in particular 2:1.2:0.5 to 2:0.4:0.08, for example 2:0.8:0,4 to 2:0.45:0.08.

The indicated mixture can additionally contain a compound of the formula (Id)

and/or a compound of the formula (Ie)

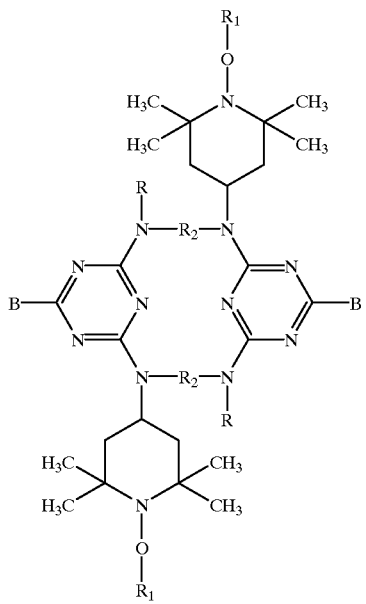

(Ie)

Each of these compounds may be present in the mixture in an amount of 0.5–30 mol %, preferably 0.5–20 mol %, 0.5–10 mol % or 0.5–8 mol %, relative to the total mixture.

Another particularly preferred mixture with a polydispersity of, for example, 1.1 to 1.7 contains the compounds of the formulae (Ia), (Ib) and (Ic) wherein $R_1$ is methyl, octyl or cyclohexyl;

$R_2$ is $C_2$–$C_6$alkylene;

A is —$N(R_4)(R_5)$ or a group of the formula (II) with $R_1$ being as defined above;

$R_4$ and $R_5$, which are identical or different, are hydrogen, $C_1$–$C_8$alkyl, 2-hydroxyethyl or 2-methoxyethyl or —$N(R_4)(R_5)$ is additionally 4-morpholinyl;

X is $NR_6$;

$R_6$ is $C_1$–$C_4$alkyl;

R is a group of the formula (IV) with $R_1$ being as defined above; and the radicals B and B* have independently of one another one of the meanings given for A.

A and B*, which are identical or different, are preferably —$N(C_1$–$C_8$alkyl$)_2$ or a group

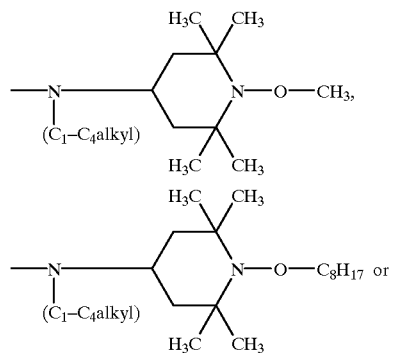

-continued

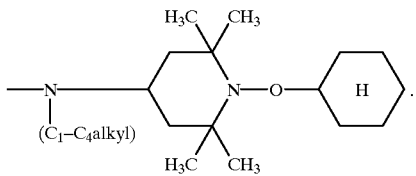

A further mixture of interest with a polydispersity of, for example, 1.1 to 1.7 contains the compounds of the formulae (Ia), (Ib) and (Ic) wherein $R_1$ is methyl, octyl or cyclohexyl;

$R_2$ is hexamethylene,

A and B* are dibutylamino;

B is N-(1-methoxy-2,2,6,6-tetramethyl-4-piperidyl)butylamino, N-(1-octyloxy-2,2,6,6-tetramethyl-4-piperidyl)butylamino or N-(1-cyclohexyloxy-2,2,6,6-tetramethyl-4-piperidyl)butylamino; and R is 1-methoxy-2,2,6,6-tetramethyl-4-piperidyl, 1-octyloxy-2,2,6,6-tetramethyl-4-piperidyl or 1-cyclohexyloxy-2,2,6,6-tetramethyl-4-piperidyl.

A further embodiment of this invention is a method for preparing a mixture having the polydispersity indicated above and containing at least three different monodispers compounds of the formula (I), which comprises 1) reacting a compound of the formula (A)

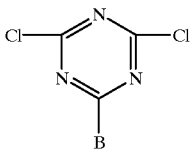

(A)

with a compound of the formula (B)

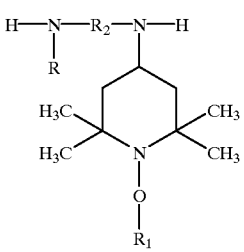

(B)

in a stoichiometric ratio to obtain a compound of the formula (C):

(C)

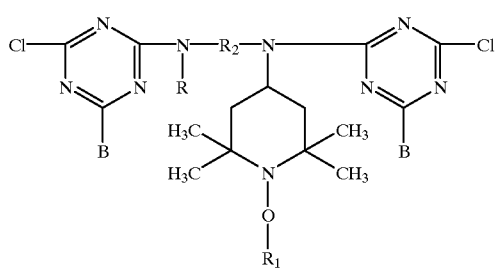

2) reacting a compound of the formula (C) with a compound of the formula (B) in a molar ratio of 1:2 to 1:3, preferably 1:2, to obtain a mixture of at least three different monodispers compounds of the formula (D) with n being 2, 3, 4, 5, 6, 7, 8, 9, 10, 11, 12, 13 or 14, in particular 2, 4 and 6;

(D)

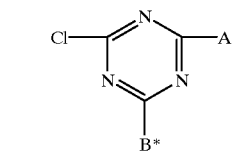

3) reacting the mixture obtained in 2) with a compound of the formula (E)

(E)

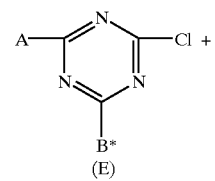

in a stoichiometric ratio to obtain the desired mixture; the reactions 1) to 3) being carried out in an organic solvent in the presence of an inorganic base.

Examples for suitable organic solvents are toluene, xylene, trimethylbenzene, isopropylbenzene, diisopropylbenzene and essentially water-insoluble organic ketones such as for example methyl ethyl ketone and methyl isobutyl ketone. Xylene is preferred.

Examples for an inorganic base are sodium hydroxide, potassium hydroxide, sodium carbonate and potassium carbonate. Sodium hydroxide is preferred. When the radical B or B" in the formula (A) or (E) is a group of the formula (II) with X being —O—, it is appropriate to use sodium carbonate or potassium carbonate as an inorganic base.

The reaction 1) is carried out, for example, at a temperature of 40° C. to 70° C., preferably 50° C. to 60° C.

The reaction 2) is carried out, for example, at a temperature of 110° C. to 180° C., preferably 140° C. to 160° C.

The reaction 3) is carried out, for example, at a temperature of 110° C. to 180° C., preferably 140° C. to 160° C.

Possible by-products are the above shown compounds of the formulae (Id) and (Ie).

The compound of the formula (A) can be prepared, for example, by reacting cyanuric chloride with a compound B-H in a stoichiometric ratio in the presence of an organic solvent and an inorganic base.

Furthermore, the compound of the formula (E) can be prepared, for example, by reacting cyanuric chloride with compounds of the formulae A-H or B*-H in a stoichiometric ratio in the presence of an organic solvent and an inorganic base.

It is appropriate to use for the preparation of the compounds of the formulae (A) and (E) the same solvent and the same inorganic base than in the above indicated reactions 1) to 3).

In general, the starting materials used in the above process are known. In the case that they are not commercially available, they can be prepared analogously to known methods. The preparation of some starting materials is described herein later.

An embodiment of this invention is also a mixture obtainable by the above indicated method.

The intermediates of the formula (D) are novel and are a further embodiment of this invention. In addition, this invention relates to a mixture containing at least three different monodispers ($\overline{M}w/\overline{M}n=1$) compounds of the formula (D) which vary only by the variable n, said mixture having a polydispersity $\overline{M}w/\overline{M}n$ of 1.1 to 1.7.

The preferred embodiments of the variable n and the radicals R, $R_1$, $R_2$ and B indicated above for the compounds of the formula (I) also relate to the intermediates of the formula (D).

A compound of the formula (I) or (D) with a polydispersity $\overline{M}w/\overline{M}n$ of 1 may be prepared by building up said compound step by step. Some representative examples for such a procedure are shown below.

I) A compound of the formula (I) wherein R is a group of the formula (IV) and n is 2 may conveniently be prepared by reacting a compound of the formula (E) with a large excess of a compound of the formula (B) to obtain a compound of the formula (F) according to Scheme I-1. The molar ratio of the compound of the formula (E) to the compound of the formula (B) may be for example 1:4.

Scheme I-1:

A—[triazine]—Cl +

B*
(E)

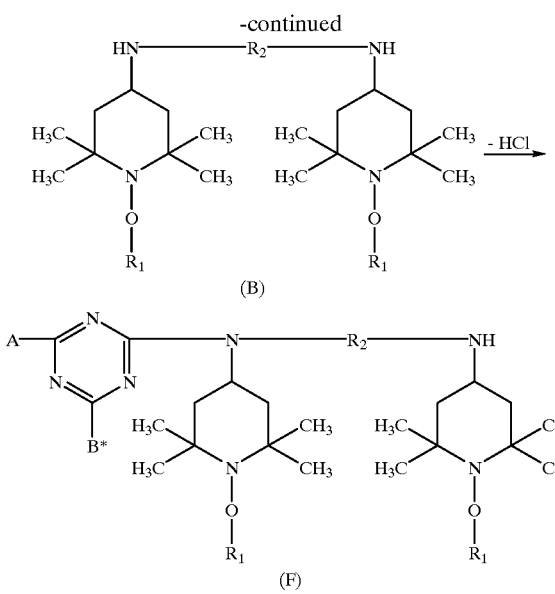

(B)

(F)

Subsequently, the compound of the formula (F) may be reacted with the compound of the formula (C) in a stoichiometric ratio to obtain the desired compound as shown in Scheme I-1.

II) A compound of the formula (I) wherein R is a group of the formula (IV) and n is 3 may conveniently by prepared by reacting a compound of the formula (F) with a compound of the formula (A) in a stoichiometric ratio to obtain a compound of the formula (G) according to Scheme II-1.

Scheme II-1:

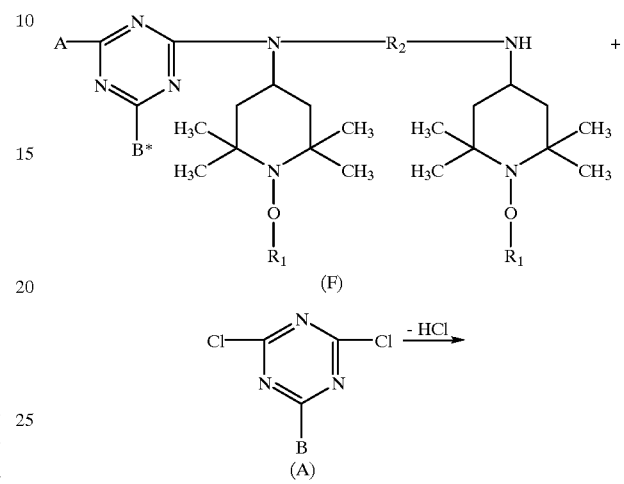

Scheme I-2:

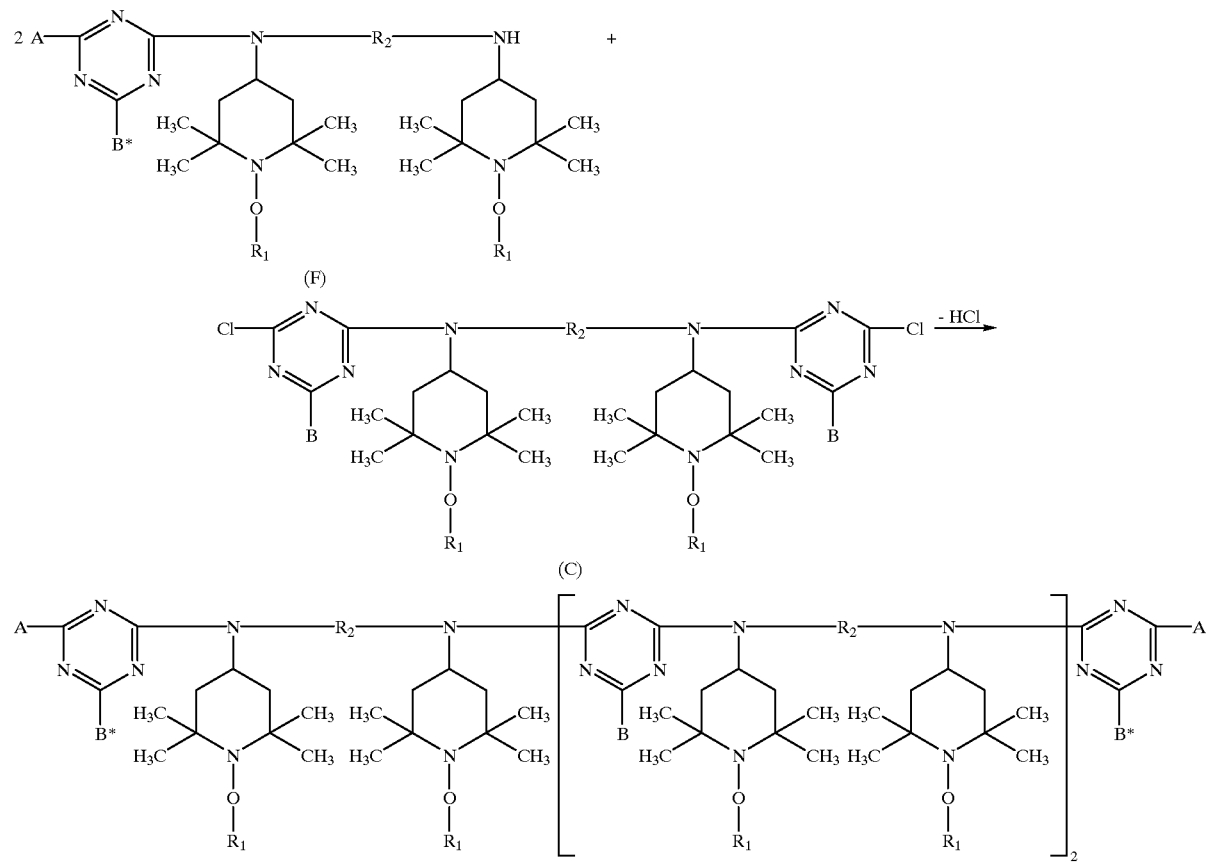

-continued
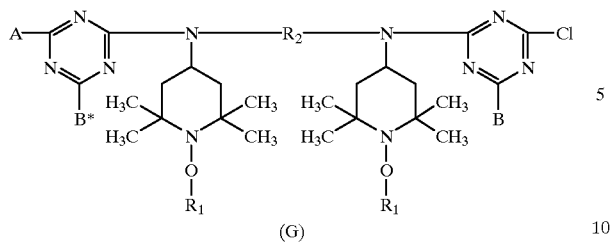
(G)
Then, the compound of the formula (G) may be reacted with a large excess of a compound of the formula (B) to obtain a compound of the formula (H) as shown in Scheme II-2. The molar ratio of the compound of the formula (G) to the compound of the formula (B) may be for example 1:4.
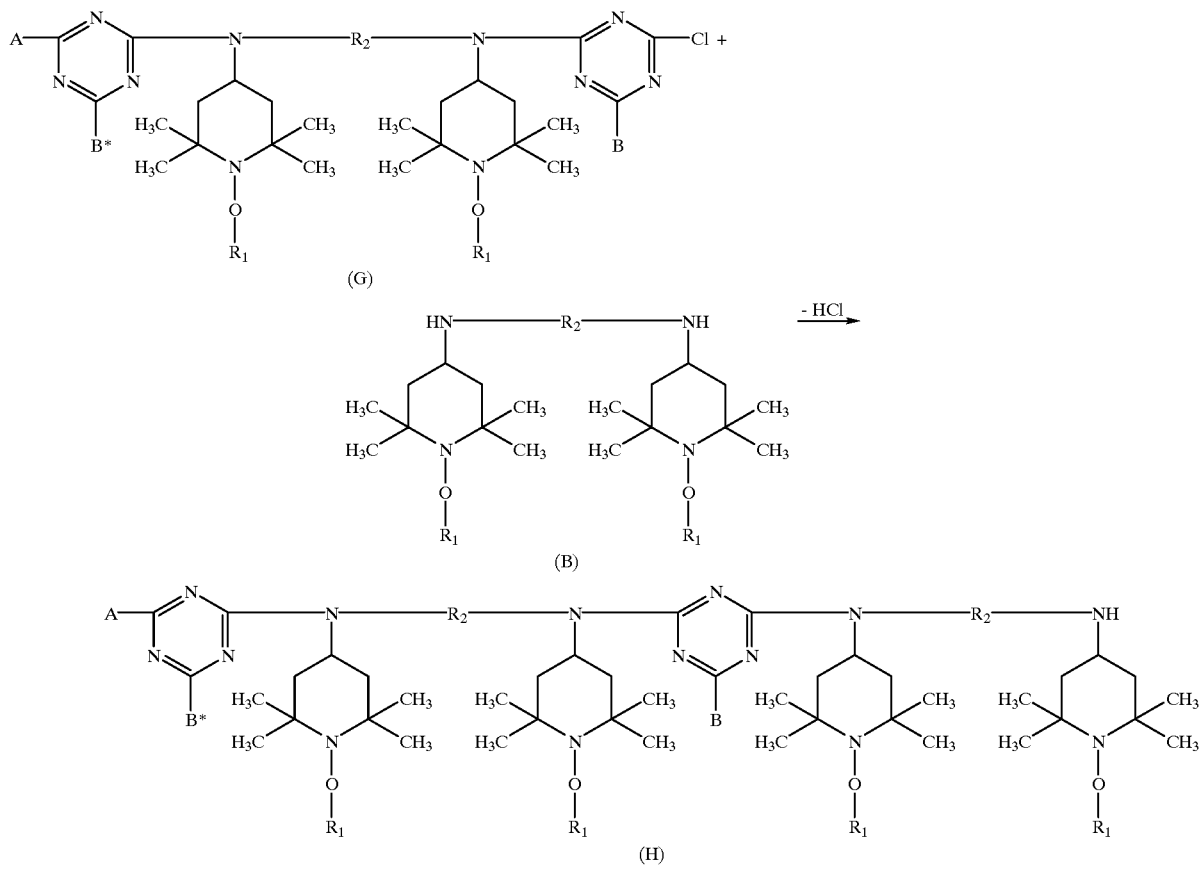

Subsequently, the compound of the formula (H) may be reacted with a compound of the formula (A) in a stoichiometric ratio to obtain a compound of the formula (K), following the Scheme II-3.

Scheme II-3:

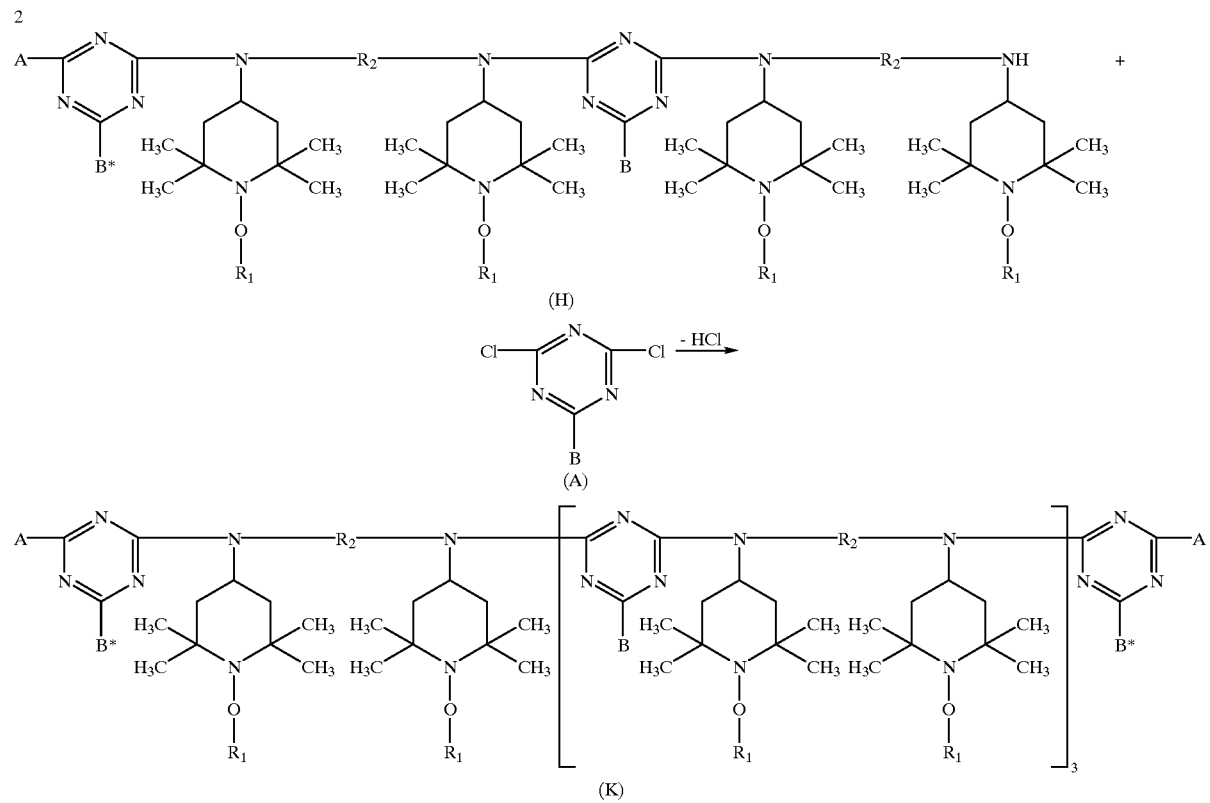

III) A compound of the formula (I) wherein R is a group of the formula (IV) and n is 4 may conveniently be prepared by reacting a compound of the formula (H) with a compound of the formula (C) in a stoichiometric ratio to obtain a compound of the formula (L).

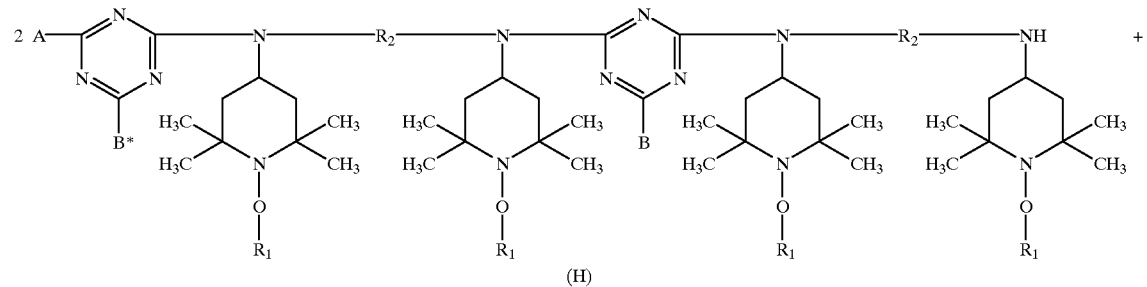

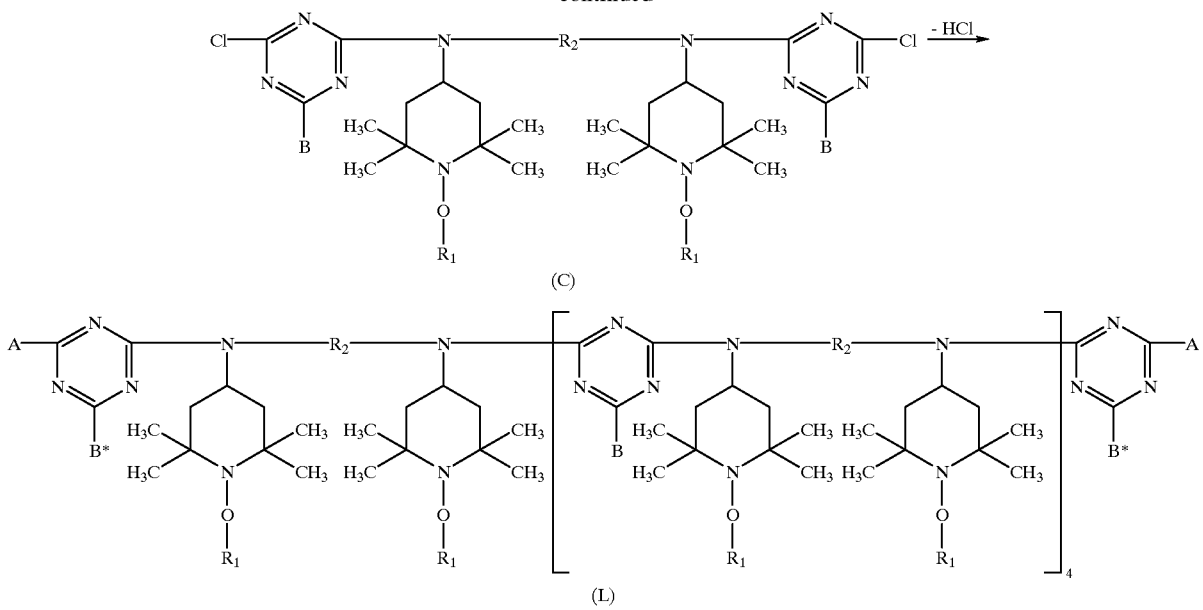

(C)

(L)

The reactions I) and III) are carried out, for example, in an organic solvent such as toluene, xylene, trimethylbenzene in the presence of an inorganic base such as sodium hydroxide at a temperature of 110° C. to 180° C., preferably 140° C. to 160° C.

The intermediate of the formula (D) wherein n is for instance 2 and which has a polydispersity $\overline{M}n/\overline{M}n$ of 1 may be prepared, for example, by reacting a compound of the formula (C) with a compound of the formula (B) in a molar ratio of 1:10 to 1:50, preferably 1:20 to 1:40, in particular 1:20 to 1:35. The reaction may be carried out e.g. in an organic solvent or neat in the presence of an inorganic base. The solvent and/or the excess of the reactant of the formula (B) can be eliminated by distillation at the appropriate conditions. Examples for an organic solvent are toluene, xylene, trimethylbenzene, isopropylbenzene and diisopropylbenzene. Xylene is preferred. Examples for an inorganic base are sodium hydroxide, potassium hydroxide, sodium carbonate and potassium carbonate. Sodium hydroxide is preferred. The reaction is carried out at a temperature of, for example, 110° C. to 180° C., preferably 140° C. to 160° C.

The compounds of the formula (I) as well as the described mixtures with a narrow molecular weight distribution are very effective in improving the light, heat and oxidation resistance of organic materials, especially synthetic polymers and copolymers. In particular, a low pigment interaction as well as a very good colour is observed in polypropylene, especially polypropylene fibres, in particular in the presence of flame retardants as well as in low density polyethylene (LDPE) films for agricultural uses. It is further remarkable that the compounds of the formula (I) as well as the described mixtures with a narrow molecular weight distribution are flame retardants themselves.

Examples of organic materials which can be stabilized are:
1 Polymers of monoolefins and diolefins, for example polypropylene, polyisobutylene, polybut-1-one, poly-4-methylpent-1-one, polyisoprene or polybutadiene, as well as polymers of cycloolfins, for instance of cyclopentene or norbomene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalysts systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene-1-ene copolymers, ethylene/hexane copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene of $\alpha$-methylstyrene with dienes or acrylic derivatives, for example styrene/butadiene, styrene/acrylonitrile, styrene/alkyl methyacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers or styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates in the other, as well as precursors thereof.

16. Polyamides and copolyamides derived from diamines and dicarboxylic acids and/or from aminocarboxylic acids of the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of diglycidyl ethers or bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.

The invention thus also relates to a composition comprising an organic material susceptible to degradation induced by light, heat or oxidation and at least one compound of the formula (I). The totally of the compounds of the formula (I) being present in the composition has preferably a polydispersity $\overline{M}w/\overline{M}n$ of 1 to 1.7, for example 1 to 1.65, 1 to 1.6 to 1 to 1.55.

The invention further relates to a composition comprising an organic material susceptible to degradation induced by light, heat or oxidation and a mixture containing at least three different monodispers ($\overline{M}w/\overline{M}n=1$) compounds of the formula (I) which vary only by the variable n, said mixture having a polydispersity $\overline{M}w/\overline{M}n$ of 1.1 to 1.7 or 1.1 to 1.6, with the proviso that the totality of the compounds of the formula (I) being present in the composition has a polydispersity $\overline{M}w/\overline{M}n$ of 1.1 to 1.7 or 1.1 or 1.6.

The organic material is preferably a synthetic polymer, more particularly one selected from the aforementioned groups. Polyolefins are preferred and polyethylene and polypropylene are particularly preferred.

A further embodiment of this invention is a method for stabilizing an organic material against degradation induced by light, heat or oxidation, which comprises incorporating into said organic material at least one compound of formula (I). The totally of the compounds of of the formula (I) being present in the composition has preferably a polydispersity $\overline{M}w/\overline{M}n$ of 1 to 1.7, in particular 1 to 1.6.

The compounds of the formula (I) or a mixture thereof can be used in various proportions depending on the nature of the material to be stabilized, on the end use and on the presence of other additives.

In general, it is appropriate to use, for example, 0.01 to 5% by weight of the compounds of the formula (I) or the mixture thereof, relative to the weight of the material to be stabilized, preferably 0.05 to 2%, in particular 0.05 to 1%.

The compounds of the formula (I) or the mixture thereof can be added, for example, to the polymeric materials before, during or after the polymerization or crosslinking of the said materials. Furthermore, they can be incorporated in the polymeric materials in the pure form or encapsulated in waxes, oil or polymers.

The materials stabilized with the compounds of the formula (I) or the mixture thereof can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the organic materials containing the compounds of the formula (I) or mixtures thereof.

Particular examples of said conventional additives are:
1. Antioxidants
   1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
   1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
   1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenol) adipate.
   1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis [2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis-(3,5-di-tert-butyl-4-hydroxyphenyl)propane, 2,2-bis(5-tert-butyl-4-hydroxy2-methylphenyl)-4-n-dodecylmercaptobutane, 1,1,5,5-tetra-(5-tert-butyl-4-hydroxy-2-methylphenyl) pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetae, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,4-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenyl)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example, dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilde, octyl N-(3,5-di-tert-butyl-4-hydroxyphenyl) carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanaurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trixabicyclo[2.2.2]octane.

1.14. Esters of β(5-tert-butyl-4-hydroxy-3-methylphenyl) propionic acid with mono- or polyhydric alcohols, e.g with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tertbutyl-4-hydroxyphenylpropionyl) hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis [2-(3-[3,5-di-tert-butyl-4-hydroxyphenyl]propionyloxy)ethyl] oxamide (Naugard®XL-1 supplied by Uriroyal).

1.18. Ascorbic acid (vitamin C)

1.19. Aminic antioxidants, for example N,N'-di-isopropyl-p-phenylenediamine, N,N''-di-secbutyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimetthylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-toly) biguanide, bis[4-(1'3'-dimethylbutyl)phenyl]amine, tertoctylated N-phenyl-1-naphthylamine, a mixture of mono- and dialkylated tert-butyl/tertoctyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkyhlated tert-octyl-phenothiazines, N-allylphenothiazin, N,N,N',N'-tetraphenyl-1,4-diaminobut-2-ene, N,N-bis-2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3'5'-di-tert-butyl-2'-hydroxyphenyl)benzotriazole, 2-(5'-tert-butyl-2'-hydroxyphenyl) benzotriazole, 2-(2'-hydroxy-5'-(1,1,3,3-tetramethylbutyl)phenyl) benzotriazole, 2-(3'5'-ditert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5=-di-tert-amyl-2'-hydroxyphenyl)benzotriazole, 2-(3',5'-bis-(α,α-dimethylbenzyl)-2'-hydroxyphenyl) benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxy-carbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole, 2-(3'-tert-butyl-2'-hydroxy-)5'-(2-isoctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$$\frac{}{}_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl) phenyl]benzotriazole.

2.2. 2-Hydroxybenzophenones, for example the 4-hydroxy, 4-methoxy, 4-oxtyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenylsalicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-ββ-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl) phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3, 5-di-tertbutylbenzylphosphonic acid, nickel complexes of ketoximines, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6, 6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tertbutylbenzyl) malonate, 3-n-octyl-7,7,9,9-tetramethyl-1,3,8-triazaspiro[4.5]decan-2,4-dione, bis (1-octyloxy-2,2,6,6-tetramethylpiperidyl)sebacate, bis (1-octyloxy-2,2,6,6-tetramethylpiperidyl) succinate, linear or cyclic condensates of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino) ethane, the condensate of 2-chloro-4,6-di-(4-nbutylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl) hexamethylenediamine and 4-cyclohexylamino-2,6-dichloro-1,3,5-triazine, a condensation product of 1,2-bis(3-aminopropylamino) ethane and 2,4,6-trichloro-1,3,5-triazine as well as 4-butylamino-2,2,6,6-tetramethylpiperidine (CAS Req. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl) ethene, N,N'-bisformyl-N,N'-bis(2,2,6,6-tetramethyl-4-piperidyl) hexamethylenediamine, diester of 4-methoxymethylene-malonic acid with 1,2,2,6,6-pentamethyl-4-hydroxypiperidine, poly(methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanalide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-oxtyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-2,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy) phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris [2-hydroxy-4-(3-butoxy-2-hydroxy-propoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloy) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis (salicyloyl)thiopropionyl dihydrazide.

4. Phosphites and phosphorites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-diphosphite, bis(2,4-di-tert-butyl-6-methylphenyl) pentaerythritol diphosphite, bis(2,4,6-tris (tertbutylphenyl) pentaerythritol diphosphite, tristearyl sorbitol triphosphite, tetrakis(2,4-di-tert-butylphenyl) 4,4'-biphenylene diphosphorite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tertbutyl-6-methylphenyl) ethyl phosphite, 2,2',2"-nitrilo[triethyltris (3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite.

5. Hydroxylamine, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecylalpha-heptadecyl-nitrone, N-octadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7-thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto) propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine drivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; De-A-4316611; DE-A-4316622; De-A-4316876; EP-A-0589839 or EP-A-0591102 or 3-[4-(2-acetoxyethoxy)phenyl]-5,7-di-tert-butyl-)benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,6-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The weight ratio of the compounds of the formula (I) or the mixture thereof to the conventional additives may be 1:0.5 to 1:5.

The compounds of the formula (I) or mixtures thereof are particularly useful for stabilizing pigmented polyolefins, in particular polypropylene.

The compounds of the formula (I) or mixtures thereof can also be used as stabilizers, especially as light stabilizers, for almost all materials known in the art of photographic reproduction and other reproduction techniques as e.g. described in Research Disclosure 1990, 31429 (pages 474 to 480).

The explanations and comments given above for the compounds of the formula (I) and mixtures thereof with regard to the stabilization of organic materials are also applicable to the intermediates of the formula (D) and mixtures thereof.

The invention is illustrated in more detail by the following Examples. All percentages are by weight, unless otherwise indicated. The compounds of the Examples V-1 and V-2 relate to a particular preferred embodiment of this invention.

The starting materials of the formula (I-S)

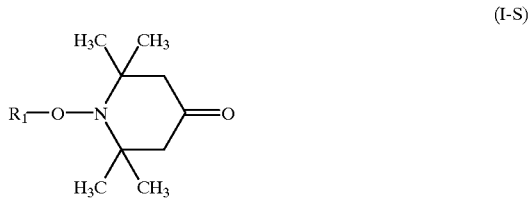

(I-S)

may be prepared, for example, by reacting 1-oxyl-2,2,6,6-tetramethyl-4-piperidone with a hydroperoxide, preferably t-butyl hydroperoxide, in the presence of a peroxide decomposing catalyst such as $MoO_3$ in a hydrocarbon solvent. The meaning of $R_1$ depends on the hydrocarbon solvent used. For example, when $R_1$ is cyclohexyl, the hydrocarbon solvent used is cyclohexane. In general, the preparation of the starting materials of the formula (I-S) may be carried out analogously to the process described in U.S. Pat. No. 4,921,962 which is incorporated herein by reference.

It is also possible to prepare the compounds of the formula (I-S) by coupling 1-oxyl-2,2,6,6-tetramethyl-4-piperidone with hydrocarbon radicals. The principle of such a reaction is, for example, described by R. L. Kinney et al. in J. Am. Chem. Soc., 1978, 100, 7902–7915 (Reaction of alkyl iodides with tri-n-butyltin hydride) and by D. W. Grattan at al. in Polym. Degrad. and Stability 1979, 69 (Photolysis of a solution of di-tertbutyl peroxide and cyclohexane). The indicated reactions are, example, disclosed in U.S. Pat. No. 5,021,577 (Examples 5 and 16) as well as in U.S. Pat. No. 5,204,473 (Examples 7 to 10) and can be applied to prepare the compounds of the formula (I-S) by using the appropriate starting materials.

When $R_1$ is methyl, the preparation of the compound of the formula (I-S) is conveniently carried out by reacting 1-oxyl-2,2,6,6-tetramethyl-4-piperidone with hydrogen peroxide in the presence of ferrous sulfate heptahydrate in dimethylsulfoxide, as disclosed for example in U.S. Pat. No. 5,374,729.

The preparation of 1-oxyl-2,2,6,6-tetramethyl-4-piperidone is, for example, described in Nature 196, 472–474, Chemical Abstracts 58: 56264 and Beilstein EIII/IV 21 3279.

Compounds of the formula (I) wherein $R_1$ is hydrogen may be prepared for example by hydrogenation of compounds of the formula (I) wherein —O—$R_1$ is oxyl. The hydrogenation can be carried out according to known methods, for example in an organic solvent, e.g. methanol or ethanol, in the presence of a hydrogenation catalyst, preferably palladium on carbon or $PtO_2$, as described e.g. in U.S. Pat. No. 4,691,015.

The following Examples I-1 and I-2 illustrate the preparation of the starting materials of the formula (I-S) more specifically.

EXAMPLE I-1

Starting Material

Preparation of 1-methoxy-2,2,6,6-tetramethyl-4-piperidone

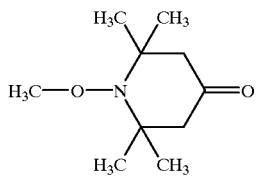

A 5.0 L 4 neck mechanically stirred flask is charged with 1oxyl-2,2,6,6-tetramethyl-4-piperidone (300 g, 1.76 moles), ferrous sulfate heptahydrate (513.7 g, 1.85 moles) and dimethylsulfoxide (1450 g). Hydrogen peroxide, 30% (279.2 g, 2.46 moles), is added over a 1 hour 45 min span. The temperature is maintained at 29–32° C. The Content is stirred for an additional 30 min at 25–30° C. and then chilled below 10° C. Water (1250 ml) is added and the mixture is extracted with four 750 ml portions of ethyl acetate. The combined extracts are washed, 2×1.0 L of $H_2O$, then 1×500 ml of saturated NaCl and then dried over anhydrous $MgSO_4$. Ethyl acetate is evaporated and the product is distilled (82–84° C./0.33×10$^{-2}$ bar), yielding 254 g of a pale yellow oil (yield: 78% of theory; IR-spectrum: Ketone carbonyl, 1710 cm–1).

EXAMPLE I-2

Starting Material

Preparation of 1-cyclohexyloxy-2,2,6,6-tetramethyl-4-piperidone

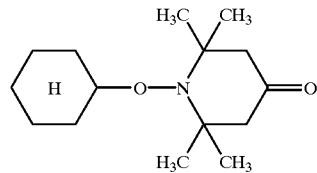

A mixture of cyclohexane (215 ml, 2.0 moles), t-butyl hydroperoxide, 70% aqueous (77.1 g, 0.6 moles), molybdenum trioxide (1.44 g, 0.01 moles) and 1-oxyl-2,2,6,6-tetramethyl-4-piperidone (34 g, 0.2 moles) is charged into a 500 ml flask equipped with a Barrett trap. The mixture is stirred at reflux (80° C.) for two hours until no more water is collected. Then, the mixture is filtered by gravity into a pressure bottle and molybdenum trioxide (1.44 g, 0.01 mole) are added. Subsequently, the mixture is heated under stirring to 105° C. (2.34 bar) and held for 5 hours, until the color changes from deep orange to pale yellow. The mixture is filtered and the clear solution is washed with 10% aqueous sodium sulfite (100 ml) and subsequently with water (2×50 ml). The obtained clear solution is dried over sodium sulfate and then concentrated to give 50 g of the desired material as a clear yellow oil (Mass spectrum: m/e=253)

The starting materials of the formula (II-S)

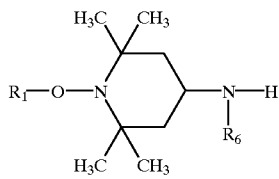

(II-S)

may be prepared, for example, analogously to the following Examples II-1 and II-2.

EXAMPLE II-1

Starting Material

Preparation of N-(1-methoxy-2,2,6,6-tetramethyl-4-piperidyl)butylamine

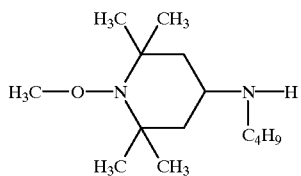

A mixture of 185.3 g (1 mole) of 1-methoxy-2,2,6,6-tetramethyl-4-oxopiperidine and 76.8 g (1.05 moles) of n-butylamine in 200 ml of methanol is added to 0.3 g of Pt/C (5% w/w) moistened with 50% (% w/w) of water.

The mixture is maintained under stirring and under $N_2$ atmosphere for 2 hours and hydrogenated in an autoclave at 50° C. and a hydrogen pressure of 10 bar.

After completion of the hydrogen absorption, the mixture is filtered and the solvent is evaporated off under vacuum (50° C./3 mbar). Subsequently, the oily residue is distilled at 94–99° C./0.4 mbar.

EXAMPLE II-2

Starting Material

Preparation of N-(1-cyclohexyloxy-2,2,6,6-tetramethyl-4-piperidyl)butylamine

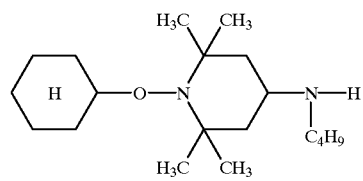

The product is prepared analogously to the method described in Example II-1, by reaction of 126.7 g (0.5 moles) of 1-cyclohexyloxy-2,2,6,6-tetramethyl-4-oxopiperidine and 38.4 g (0.52 moles) of n-butylamine.

An oily product is obtained which is separated as hydrate (=wax with a melting point of <30° C.).

The starting materials of the formula (III-S)

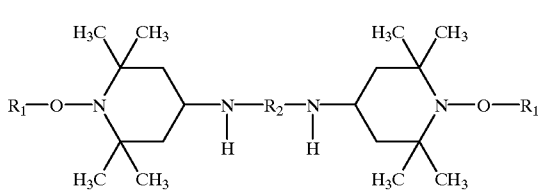

(III-S)

may be prepared e.g. analogously to the following Examples III-1 and III-2. Some diamino compounds which may be used for the preparation of the starting materials of the formula (III-S) are, for example, described in WO-A-95/21157, U.S. Pat. No. 4,316,837 and U.S. Pat. No. 4,743,688.

EXAMPLE III-1

Starting Material

Preparation of N,N'-bis(1-methoxy-2,2,6,6-tetramethyl-4-piperidyl)-1,6-hexanediamine

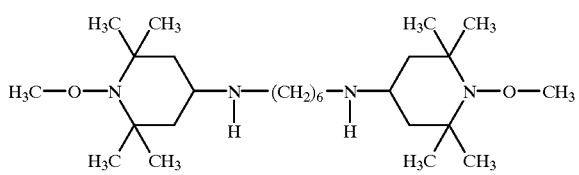

The product is prepared as described in Example II-1, by reaction of 185.3 g (1 mole) of 1-methoxy-2,2,6,6-tetramethyl-4-oxopiperidine and 60.4 g (0.52 moles) of 1,6-hexanediamine.

After crystallization from acetone, a white solid product is obtained with a melting point of 63–65° C.

EXAMPLE III-2

Starting Material

Preparation of N,N'-bis(1-cyclohexyloxy-2,2,6,6-tetramethyl-4-piperidyl)-1,6-hexanediamine

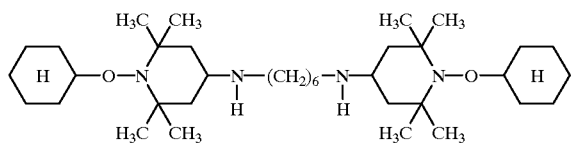

The product is prepared as described in Example II-1, by reaction of 126.7 g (0.5 moles) of 1-cyclohexyloxy-2,2,6,6-tetramethyl-4-oxopiperidine and 30.2 g (0.26 moles) of 1,6-hexanediamine.

An oily product is obtained which is separated as hydrate (=wax with a melting point of <30° C.).

The starting materials of the formula (IV-S)

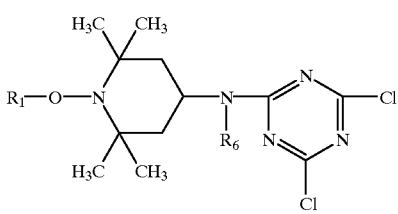

(IV-S)

may be prepared, for example, analogously to the following Examples IV-1 and IV-2.

EXAMPLE IV-1

Starting Material

Preparation of 2,4-dichloro-6-[N-(1-methoxy-2,2,6,6-tetramethyl-4-piperidyl)butylamino]-[1.3.5]-triazine

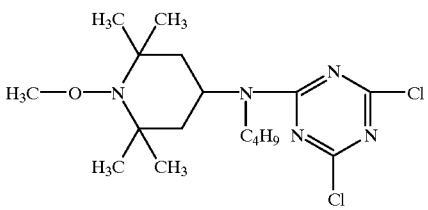

39.7 g (163 mmoles) of N-(1-methoxy-2,2,6,6-tetramethyl-4-piperidyl)butylamine are slowly added to a solution of 30 g (163 mmoles) of cyanuric chloride in 180 ml of xylene, maintained at room temperature. After the addition, the mixture is stirred for ½ hour at room temperature and subsequently, a solution of 6.8 g (170 mmoles) of sodium hydroxide in 45 ml of water is slowly added, maintaining the temperature at room temperature.

After the addition, the mixture is stirred for further 4 hours and the aqueous phase is separated off.

The xylenic solution is washed twice with 60 ml of water, dried over anhydrous sodium sulfate, filtered and concentrated under vacuum (60° C./1 mbar).

A white solid with a melting point of 109–110° C. is obtained.

Cl analysis: Calculated: 18.16% Found: 17.93%

EXAMPLE IV-2

Starting Material

Preparation of 2,4-dichloro-6-[N-(1-cyclohexyloxy-2,2,6,6-tetramethyl-4-piperidyl)butylamino]-[1.3.5]-triazine

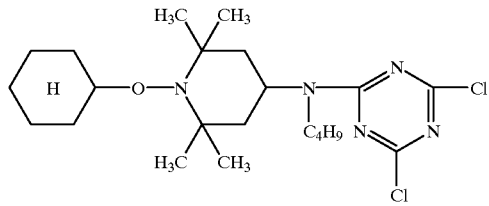

The product is prepared analogously to the method described in Example IV-1, using suitable reactants in the appropriate molar amounts.

Compounds of the formula (IV-S-1)

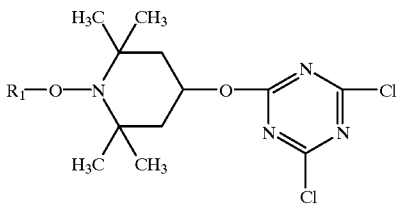
(IV-S-1)

may be prepared, for example, according to the Scheme shown below.

Scheme:

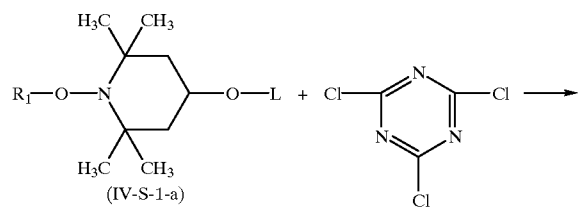

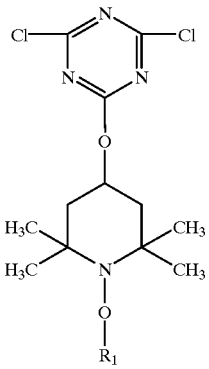

L is for example an alkaline metal salt such as lithium, sodium or potassium. The reaction may be carried out in an inert organic solvent such as toluene, xylene or trimethylbenzene at a temperature of −20° C. to 70° C., preferably 0° C. to 60° C., using the appropriate molar ratio of the reactants.

The compounds of the formula (IV-S-1-a) may be obtained, for example, by treating the appropriate 4-hydroxypiperidine derivative with an alkaline alcoholate or an alkaline metal in an inert organic solvent such as toluene, xylene or trimethylbenzene at reflux temperature, simultaneously distilling off the alcohol formed during the reaction. The preparation of the 4-hydroxypiperidine derivative can be carried out analogously to the method described in EP-A-309 402 (in particular Example 12).

GPC (Gel Permeation Chromatography) is used as an analytical procedure for separating molecules by their difference in size and to obtain molecular weight averages ($\overline{M}w$, $\overline{M}n$) or information on the molecular weight distribution of polymers.

The technique is well known and described, for instance, in "Modern Size—Exclusion Liquid Chromatography" by W. W. Yan et al., edited by J. Wiley & Sons, N.Y., USA, 1979, pages 4–8, 249–283 and 315–340.

A narrow molecular weight distribution is characterized by a polydispersity ($\overline{M}w/\overline{M}n$) close to 1.

The GPC analyses shown in the following Examples are carried out with a GPC chromatograph ®Perkin-Elmer LC 250 equipped with ®Perkin-Elmer RI detector LC 30 and with ®Perkin-Elmer oven LC 101.

All the analyses are carried out at 45° C. by using three columns PLGEL 3 μm Mixed E 300 mm length×7.5 mm i.d. (from Polymers Laboratories Ltd. Shropshire, U.K).

Tetrahydrofurane is used as eluant (flow 0.40 ml/min) and the samples are dissolved in tetrahydrofurane (2%) (% w/v).

In the structural formulae of the following examples, n' indicates that there are repetitive units in the molecules and the products obtained are not uniform. These products are characterized by the number average molecular weight $\overline{M}n$ and the polydispersity $\overline{M}w/\overline{M}n$.

EXAMPLE V-1

Preparation of the Compound of the Formula

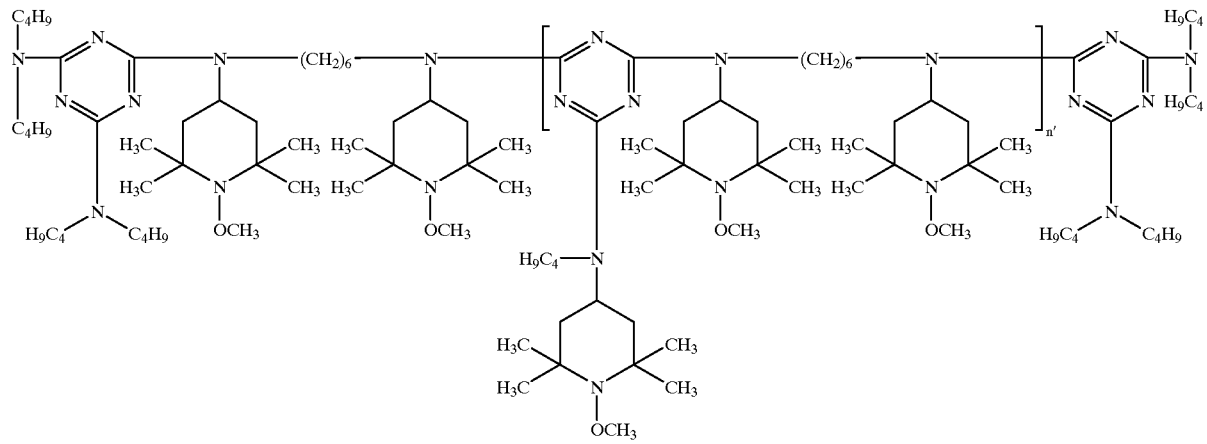

A solution of 24.4 g (53 mmoles) of N,N'-bis(1-methoxy-2,2,6,6-tetramethyl-4-piperidyl)-1,6-hexanediamine in 30 ml of xylene is slowly added to a solution of 41.3 g (106 mmoles) of 2,4-dichloro-6-[N-(1-methoxy-2,2,6,6-tetramethyl-4-piperidyl)butylamino]-1,3,5-triazine in 100 ml of xylene, under stirring at 35–40° C. Then, the mixture is heated to 60° C. and a solution of 4.6 g (115 mmoles) of sodium hydroxide in 15 ml of water is slowly added.

Subsequently, the mixture is heated to 80° C. and maintained at 80° C. for 4 hours under stirring.

The aqueous solution is separated off and 48.7 g (106 mmoles) of N,N'-bis(1-methoxy-2,2,6,6-tetramethyl-4-piperidyl)-1,6-hexanediamine and 8.5 g (212 mmoles) of ground sodium hydroxide are added. Then, the mixture is heated to reflux for 20 hours, distilling off the reaction water and the possible residual water by azeotropation. Subsequently, the mixture is cooled down to 90° C. and 30 ml of water are added together with 100 ml of xylene.

The mixture is then heated to 100° C. under stirring for 1 hour, cooled down to 80° C. and the aqueous phase is separated off.

The organic phase is washed with 40 ml of an aqueous solution of 1N HCl and with 50 ml of water and subsequently, with a solution of 2 g (50 mmoles) of sodium hydroxide in 40 ml of water.

Then, 16.8 g (45 mmoles) of 2-chloro-4,6-bis(dibutylamino)-1,3,5-triazine and 9.4 g (235 mmoles) of ground sodium hydroxide are added and the mixture is heated to reflux for 24 hours, separating off the reaction water and the possible residual water by azeotropation.

The mixture is cooled down to 60° C. and 50 ml of water are added.

After stirring for 1 hour at 60° C., the aqueous phase is separated off and the organic phase is washed once with 50 ml of water and dried over anhydrous sodium sulfate.

After filtration and evaporation under vacuum (70° C./1 mbar), a light yellow solid product is obtained with a melting point of 130–137° C.

$\overline{M}n$ (by GPC)=2501 g/mol $\overline{M}w/\overline{M}n=1.53$
The GPC analysis shows a chromatogram as in FIG. 1.

EXAMPLE V-2

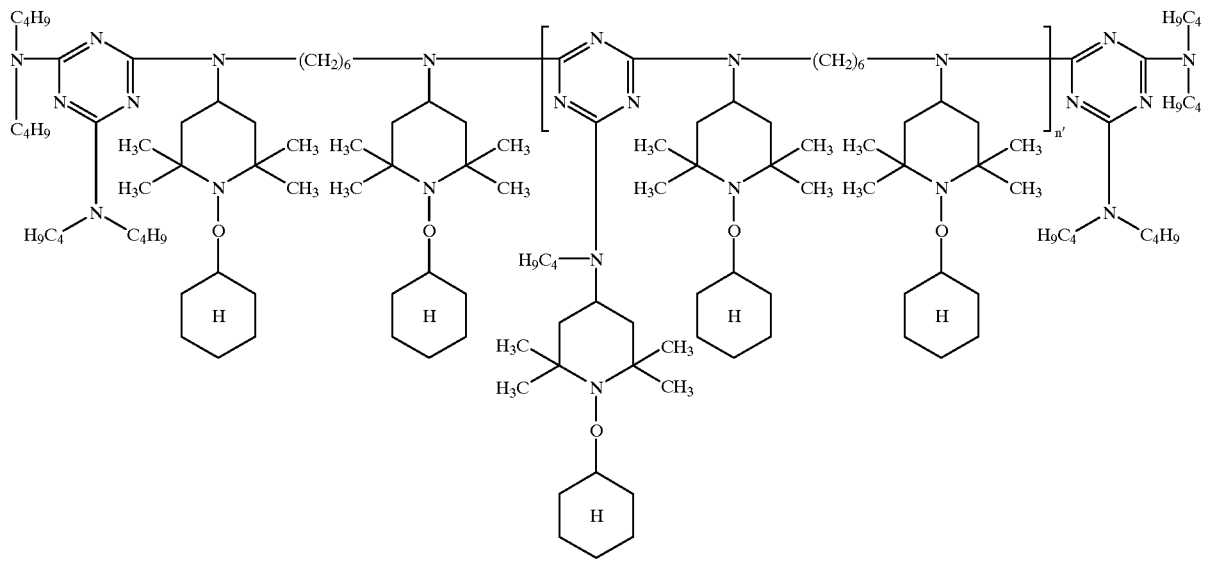

The compound is prepared analogously to the method described in Example V-1, using suitable reactants in the appropriate molar amounts.

Figure 2:
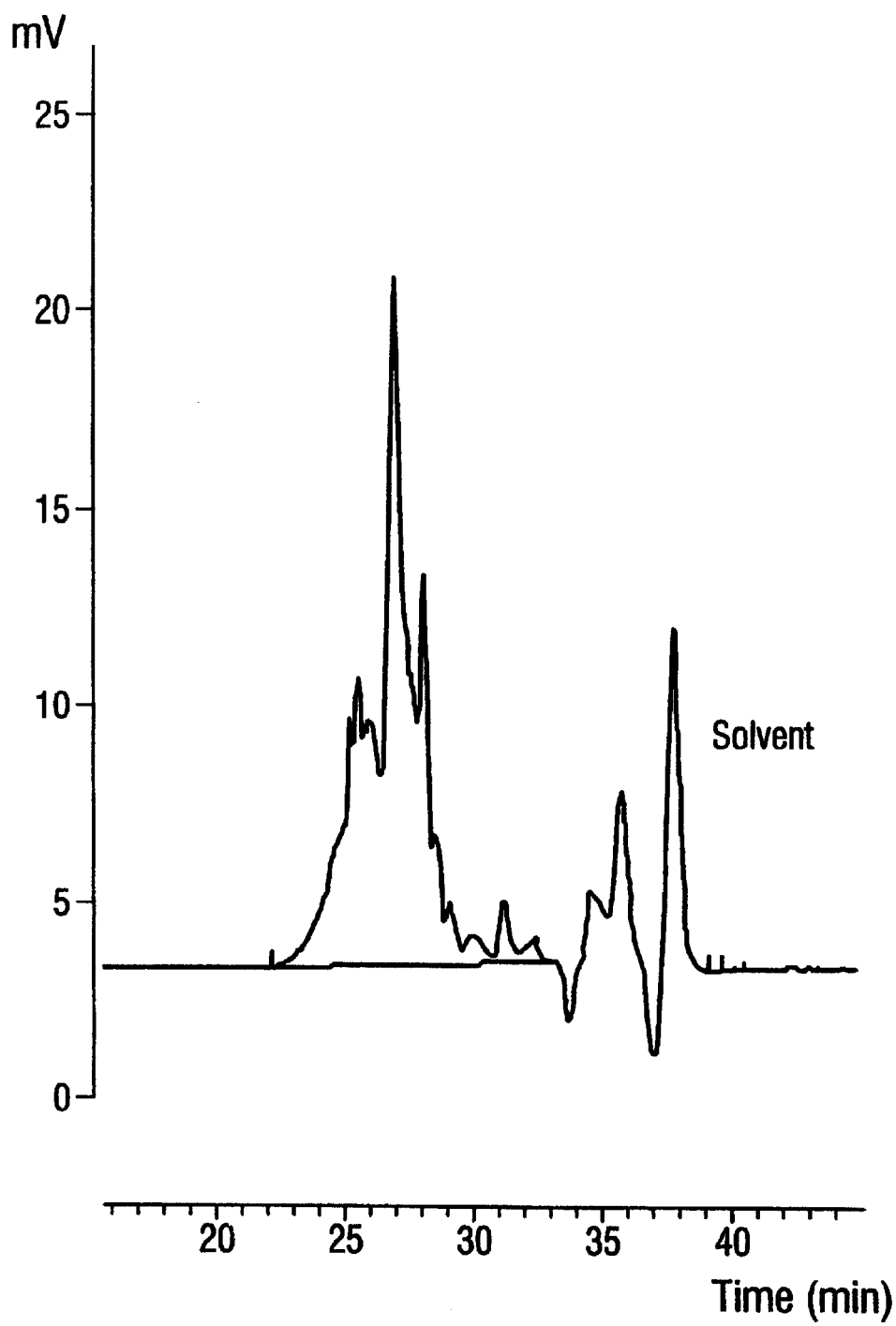

The product obtained has a melting point of 118–130° C.
$\overline{M}n$ (by GPC)=2100 g/mol
$\overline{M}w/\overline{M}n=1.35$
The GPC analysis shows a chromatogram as in FIG. 2.

A further specific example of a compound of the formula (I) which may be prepared according to the method shown above is

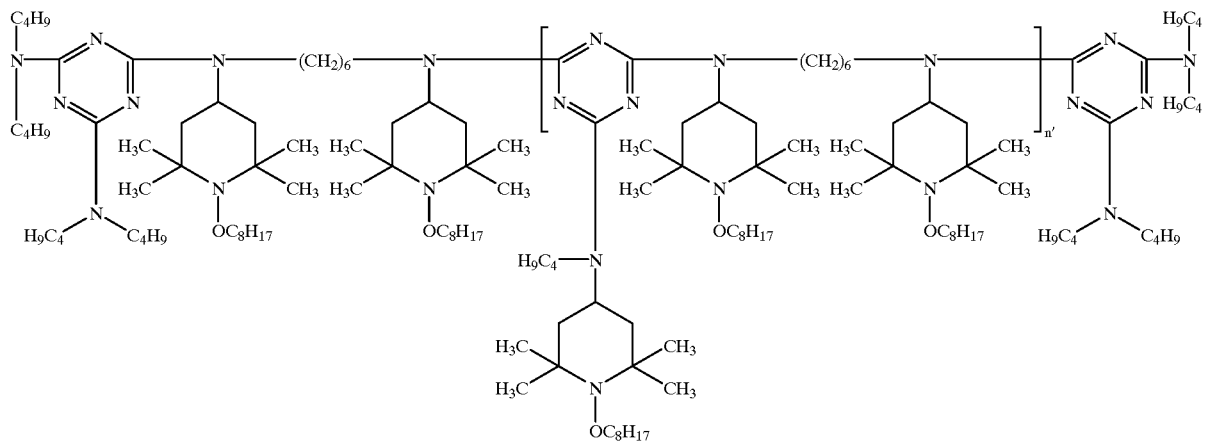

EXAMPLE A

Pigmented thermoplastic olefin (TPO) pellets are prepared by mixing a polyolefin blend (polypropylene containing an ethylene-propylene copolymer; ®Polytrope TPP 518-01 from ®A. Schulman, Inc.; Akron, Ohio, USA) with the additives listed below in a ®Superior/MPM 1" single screw extruder with a general all-purpose screw (24:1 L/D) at 200° C., cooling in a water bath and pelletizing. Prior to extrusion and molding, the additives are dry blended in a tumble dryer.

Additives:
   0.25%*⁾ of ®Red 3B (Pigment Red 177, Color Index 65300),
   0.05%*⁾ of pentaerythritol tetrakis[3-(3,5-di-tert-butyl-4-hydroxyphenyl) propionate],
   0.05%*⁾ of tris[2,4-di-tert-butylphenyl]phosphite,
   0.2%*⁾ of 2-(2'-hydroxy-3',5'-di-tert-amylphenyl) benztriazol,
   0.2%*⁾ of bis(1-octyloxy-2,2,6,6-tetramethyl-4-piperidyl) sebacate,
   0.1%*⁾ of calcium stearate,
   about 10%*⁾ of talc and
   0.2%*⁾ of the compound of Example V-1 or V-2.
*⁾ weight percent based on the polyolefin blend The resulting pellets are molded into 1.524 mm thick 2"×2" plaques at about 190° C. on a ®BOY 30M Injection Molding Machine.

The test plaques are mounted in metal frames and exposed in an ®Atlas Ci65 Xenon Arc Weather-O-meter at 70° C. black panel temperature, 0.55 W/m² at 340 nanometers and 50% relative humidity with intermittent light/dark cycles and water spray (®Society of Automotive Engineers—SAE J 1960 Test Procedure—Exterior Automotive conditions).

The specimens are tested at approximately 625 kilojoule intervals by performing color measurements on an Applied Color Systems spectrophotometer by reflectance mode according to ASTM D 2244-79. Gloss measurements are conducted on a ®BYK-GARDNER Haze/Gloss Meter at 60° according to ASTM D 523.

The stabilized samples show good gloss retention and good resistance to color change upon UV exposure.

EXAMPLE B

Greenhouse Application—Light Stabilization Properties in Low Density Polyethylene (LDPE)—Outdoor Exposure The compound of Example V-1 is mixed via master batch with LDPE pellets (Riblene® EF 2100 V, supplied by ®ENICHEM, Milano, Italy), characterized by a density of 0.921 g/cm³ and a melt flow index (190° C./2.16 kg) of 0.25, in a slow mixer.

The master batch has previously been prepared by extruding powdered LDPE and 10% by weight of the compound of Example V-1.

The mixtures are blow extruded at 200° C., and films of 150 microns thickness are obtained, containing 0.4% of the compound of Example V-1.

The films are exposed on the south-facing roof of a greenhouse in Pontecchio Marconi (Bologna, Italy) without backing, on galvanized iron backing and on pine wood backing.

The following pesticides are applied in the greenhouse:

VAPAM® (BASLINI SpA, Treviglio/BG, Italy), which is an aqueous solution of 382 g per liter of metam-sodium having the formula $CH_3$—NH—CS—SNa;

SESMETRIN® (BIMEX SpA, Isola/VI, Italy), which is a 23.75% (% w/w) aqueous solution of permethrin having the formula

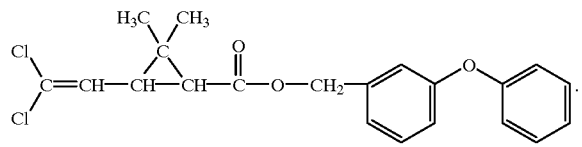

The greenhouse is treated with a solution of 4 liters of ®VAPAM in 10 liters of water every 6 months, and with ®SESMETRIN (5 g in 5 liters of water) every month.

During the exposure, the performance of the film is periodically evaluated measuring the residual elongation (in % of the initial elongation of the new LDPE film) by means of a dynamometer at constant speed.

The results reveal that the compound of Example V-1 stabilizes the LDPE film in excellent manner.

EXAMPLE C

Stabilization of Low Density Polyethylene (LDPE) Films—Outdoor Exposure

The compound of Example V-1 is mixed via master batch with LDPE pellets (Riblene® EF 2100 V, supplied by ®ENICHEM, Milano, Italy), characterized by a density of 0.921 g/cm³ and a melt flow index (190° C./2.16 kg) of 0.25, in a slow mixer.

The master batch has previously been prepared by extruding powdered LDPE and 10% by weight of the compound of Example V-1.

The mixtures are blow extruded at 200° C., and films of 150 microns thickness are obtained, containing 0.3% or 0.4% of the compound of Example V-1.

The films are exposed in Pontecchio Marconi (about 110 kLys/year) and are irradiated without support, on galvanized iron and on pine wood support, in the absence of pesticides. The films surfaces are fixed in a 45° inclination towards south.

During the exposure, the performance is periodically evaluated measuring the residual elongation (in % of the initial elongation of the new LDPE film) by means of a dynamometer at constant speed.

The results reveal that the compound of Example V-1 stabilizes the LDPE film in excellent manner.

EXAMPLE D

Fiber grade polypropylene containing 0.05% by weight of calcium stearate and 0.05% by weight of di(hydrogenated tallow) hydroxylamine as base stabilization is dry blended with the stabilizer indicated in Table 1 and then melt compounded at 234° C. into pellets. The pelletized fully formulated resin is then spun at 246° C. or 274° C. into fiber using a ®Hills laboratory model fiber extruder. The spun tow of 41 filaments is stretched at a ratio of 1:3.2 to give a final denier of 615/41.

"Socks" are knitted from the stabilized polypropylene on a ®Lawson-Hemphill Analysis Knitter and exposed in an ®Atlas Xenon-Arc-Weather-Ometer using SAE J1885 Interior Automotive conditions at 89° C. bpt, 0.55 kW/cm² at 340 nm with no spray cycle. Failure in this test is determined by the observation of the physical failure of the sock when it is "scratched" with a blunt glass rod. The longer it takes for this catastrophic failure to occur, the more effective is the stabilizer.

The results are shown in Table 1.

TABLE 1

| Stabilizer | Catastrophic Failure Time Fiber Spun at 246° C. | Catastrophic Failure Time Fiber Spun at 274° C. |
| --- | --- | --- |
| None | 192 hours | 96 hours |
| 0.25% by weight of the compound of Example V-1 | 600 hours | 600 hours |
| 0.25% by weight of the compound of Example V-2 | 600 hours | 408 hours |

What is claimed is:

1. A compound of the formula (I)

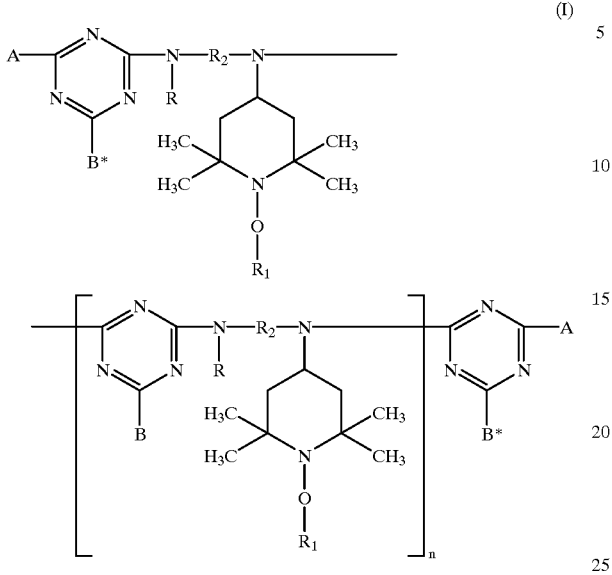

(I)

in which n is a number from 2 to 14;

the radicals $R_1$ are independently of one another hydrogen, a hydrocarbyl radical or —$OR_1$ is —O';

the radicals $R_2$ are independently of one another $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below except hydrogen;

or $R_2$ is a group of the formula (a), (b), or (c);

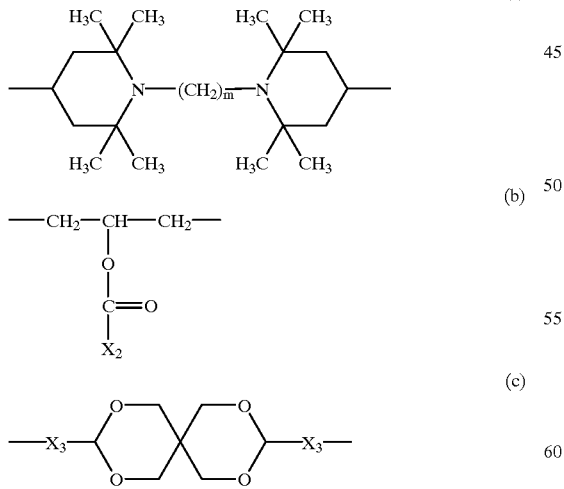

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

the radicals A are independently of one another —$OR_3$, —$N(R_4)(R_5)$ or a group of the formula (II);

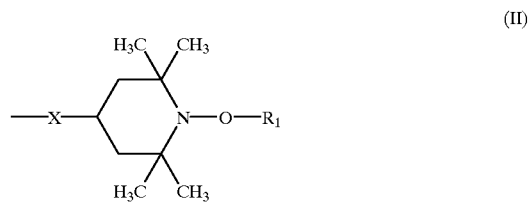

(II)

$R_3$, $R_4$ and $R_5$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

(III)

with Y being —O—, —$CH_2$—, —$CH_2CH_2$— or >N—$CH_3$, or —$N(R_4)(R_5)$ is additionally a group of the formula (III);

X is —O— or >N—$R_6$;

$R_6$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV),

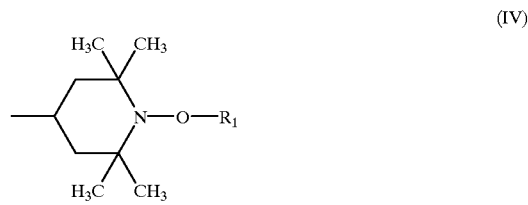

(IV)

or $C_2$–$C_4$alkyl which is substituted in the 2, 3 or 4 position by —OH, $C_1$–$C_8$alkoxy, di($C_1$–$C_4$alkyl)amino or a group of the formula (III);

the radicals R have independently of one another one of the meanings given for $R_6$; and the radicals B and B* have independently of one another one of the meanings given for A;

with the proviso that in the individual recurrent units of the formula (I), each of the radicals B, R, $R_1$ and $R_2$ has the same or a different meaning.

2. A compound of the formula (I) according to claim 1, wherein the polydispersity $\overline{M}w/\overline{M}n$ is 1 and n is 2, 3, 4, 5, 6, 7, 8, 9, 10, 11, 12, 13 or 14.

3. A compound of the formula (I) according to claim 1, wherein R is a group of the formula (IV).

4. A compound of the formula (I) according to claim 1, wherein $R_1$ is hydrogen, $C_1$–$C_{18}$alkyl, $C_5$–$C_{18}$alkenyl, $C_5$–$C_{18}$alkynyl, $C_5$–$C_{12}$cycloalkyl unsubstituted or substituted by $C_1$–$C_4$alkyl; $C_5$–$C_{12}$cycloalkenyl unsubstituted or substituted by $C_1$–$C_4$alkyl; a bicyclic or tricyclic hydrocarbyl having 6 to 10 carbon atoms or $C_7$–$C_9$phenylalkyl unsubstituted or substituted on the phenyl by $C_1$–$C_4$alkyl or —$OR_1$ is —O'.

5. A compound of the formula (I) according to claim 1, wherein $R_1$ is hydrogen, $C_1$–$C_{12}$alkyl or $C_5$–$C_8$cycloalkyl.

6. A compound of the formula (I) according to claim 1, wherein $R_1$ is $C_1$–$C_8$alkyl or cyclohexyl.

7. A compound of the formula (I) according to claim 1, wherein n is a number from 2 to 6.

8. A compound of the formula (I) according to claim 1, wherein n is a number from 2 to 12;

$R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi($C_1$–$C_4$alkylene);

$R_6$ is hydrogen, $C_1$–$C_{18}$alkyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV) or $C_2$–$C_4$alkyl which is substituted in the 2, 3 or 4 position by —OH, $C_1$–$C_8$alkoxy, di($C_1$–$C_4$alkyl)amino or a group of the formula (III); and R is a group of the formula (IV).

9. A compound of the formula (I) according to claim 1, wherein $R_2$ is $C_2$–$C_{10}$alkylene, cyclohexylene, cyclohexylenedi($C_1$–$C_4$alkylene), $C_1$–$C_4$alkylenedicyclohexylene or phenylenedi($C_1$–$C_4$alkylene);

$R_3$, $R_4$ and $R_5$, which are identical or different, are hydrogen, $C_1$–$C_{12}$alkyl, $C_5$–$C_7$cycloalkyl which is unsubstituted or substituted by 1, 2 or 3 $C_1$–$C_4$alkyl; $C_3$–$C_{12}$alkenyl, phenyl which is unsubstituted or substituted by 1, 2 or 3 $C_1$–$C_4$alkyl; benzyl which is unsubstituted or substituted on the phenyl by $C_1$–$C_4$alkyl; tetrahydrofurfuryl or $C_2$–$C_3$alkyl which is substituted in the 2 or 3 position by —OH, $C_1$–$C_4$alkoxy, di($C_1$–$C_4$alkyl)amino or a group of the formula (III); or —$N(R_4)(R_5)$ is additionally a group of the formula (III); and $R_6$ is hydrogen, $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; tetrahydrofurfuryl, a group of the formula (IV) or $C_2$–$C_3$alkyl which is substituted in the 2 or 3 position by —OH, $C_1$–$C_4$alkoxy, di($C_1$–$C_4$alkyl)amino or a group of the formula (III).

10. A compound of the formula (I) according to claim 1, wherein $R_2$ is $C_2$–$C_8$alkylene;

$R_3$, $R_4$ and $R_5$, which are identical or different, are hydrogen, $C_1$–$C_8$alkyl, cyclohexyl which is unsubstituted or substituted by methyl; $C_3$–$C_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or —$N(R_4)(R_5)$ is additionally 4-morpholinyl; and $R_6$ is hydrogen, $C_1$–$C_8$alkyl, cyclohexyl which is unsubstituted or substituted by methyl; benzyl, tetrahydrofurfuryl, a group of the formula (IV) or $C_2$–$C_3$alkyl substituted in the 2 or 3 position by —OH, $C_1$–$C_4$alkoxy, dimethylamino, diethylamino or 4-morpholinyl.

11. A compound of the formula (I) according to claim 1, wherein n is a number from 2 to 6;

$R_2$ is $C_2$–$C_6$alkylene;

A is —$N(R_4)(R_5)$ or a group of the formula (II);

$R_4$ and $R_5$, which are identical or different, are hydrogen, $C_1$–$C_8$alkyl, 2-hydroxyethyl or 2-methoxyethyl or —$N(R_4)(R_5)$ is additionally 4-morpholinyl;

X is >$NR_6$;

$R_6$ is $C_1$–$C_4$alkyl; and the radicals B and B* have independently of one another one of the definitions given for A.

12. A compound of the formula (I) according to claim 1, wherein B* is different from B and each of the radicals B, R, $R_1$ and $R_2$ has the same meaning in the individual recurring units of the formula (I).

13. A mixture containing at least three different compounds of the formula (I) according to claim 2, which vary only by the variable n, said mixture having a polydispersity $\overline{M}w/\overline{M}n$ of 1.1 to 1.7.

14. A mixture according to claim 13, said mixture having a polydispersity $\overline{M}w/\overline{M}n$ of 1.1 to 1.6.

15. A mixture containing a monodispers compound of the formula (Ia), a monodispers compound of the formula (Ib) and a monodispers compound of the formula (Ic), said compounds differing only in the number of the repetitive units,

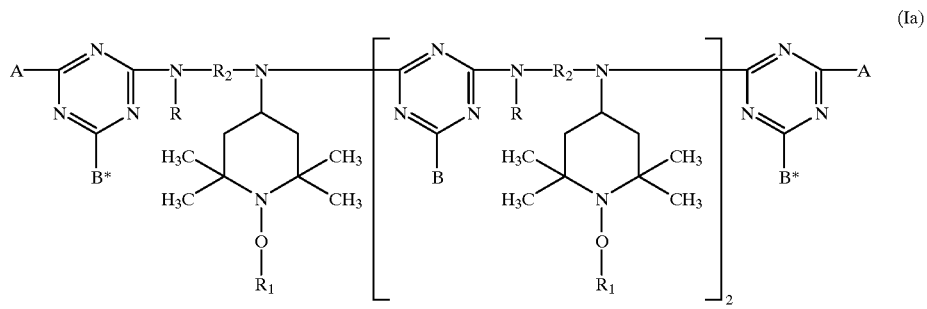

(Ia)

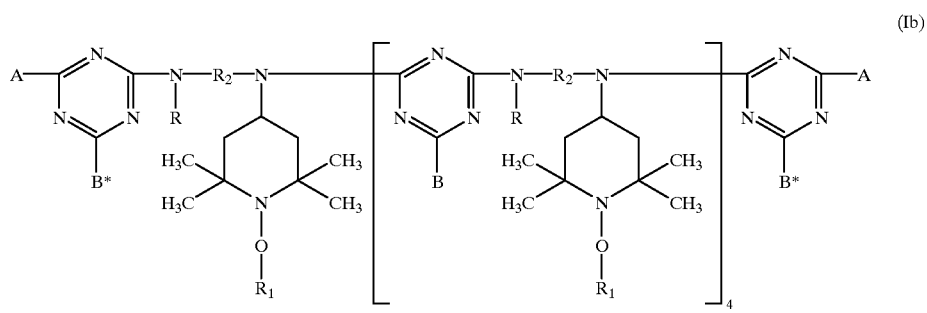

(Ib)

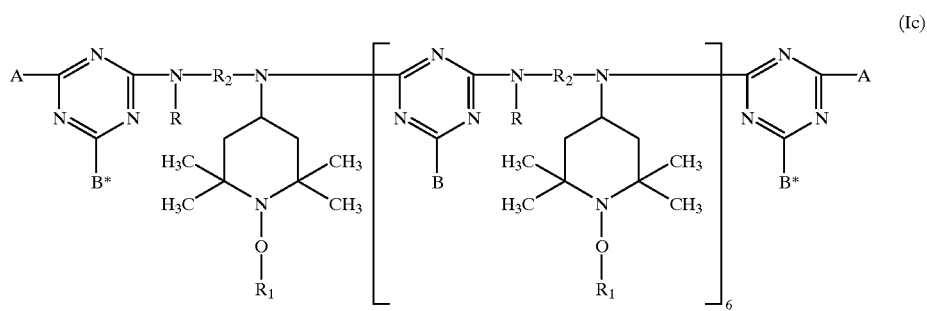

(Ic)

the radicals A, B, B*, R, $R_1$ and $R_2$ are as defined in claim 1.

16. A mixture according to claim 15, having a polydispersity $\overline{M}w/\overline{M}n$ of 1.1 to 1.7.

17. A mixture according to claim 15, wherein $R_1$ is methyl, octyl or cyclohexyl;

$R_2$ is $C_2$–$C_6$alkylene;

A is —$N(R_4)(R_5)$ or a group of the formula (II) with $R_1$ being as defined above;

$R_4$ and $R_5$, which are identical or different, are hydrogen, $C_1$–$C_8$alkyl, 2-hydroxyethyl or 2-methoxyethyl or —$N(R_4)(R_5)$ is additionally 4-morpholinyl;

X is >$NR_6$;

$R_6$ is $C_1$–$C_4$alkyl;

R is a group of the formula (IV) with $R_1$ being as defined above; and the radicals B and B* have independently of one another one of the meanings given for A.

18. A mixture according to claim 15, wherein A and B*, which are identical or different, are —$N(C_1$–$C_8$alkyl$)_2$ or a group

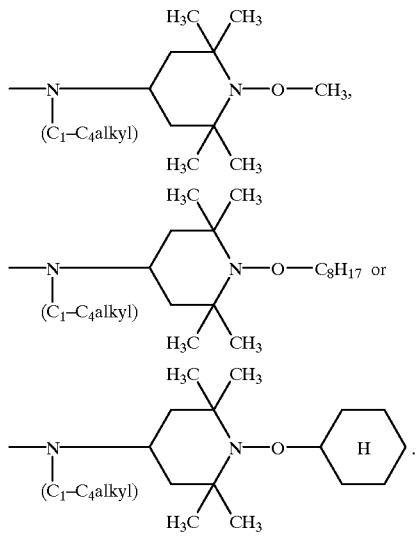

19. A mixture according to claim 15, wherein $R_1$ is methyl, octyl or cyclohexyl;

$R_2$ is hexamethylene;

A and B* are dibutylamino;

B is N-(1-methoxy-2,2,6,6-tetramethyl-4-piperidyl) butylamino, N-(1-octyloxy-2,2,6,6-tetramethyl-4-piperidyl)butylamino or N-(1-cyclohexyloxy-2,2,6,6-tetramethyl-4-piperidyl)butylamino; and R is 1-methoxy-2,2,6,6-tetramethyl-4-piperidyl, 1-octyloxy-2,2,6,6-tetramethyl-4-piperidyl or 1-cyclohexyloxy-2,2,6,6-tetramethyl-4-piperidyl.

20. A method for preparing a mixture according to claim 13, which comprises 1) reacting a compound of the formula (A)

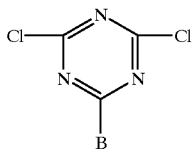
(A)

with a compound of the formula (B)

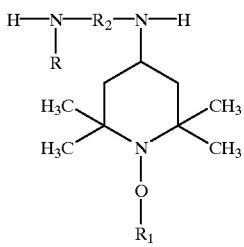
(B)

in a stoichiometric ratio to obtain a compound of the formula (C);

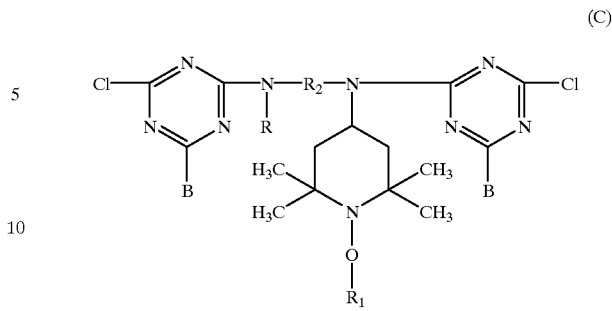
(C)

2) reacting a compound of the formula (C) with a compound of the formula (B) in a molar ratio of 1:2 to 1:3, to obtain a mixture of at least three different monodispers compounds of the formula (D) with n being 2, 3, 4, 5, 6, 7, 8, 9, 10, 11, 12, 13 or 14;

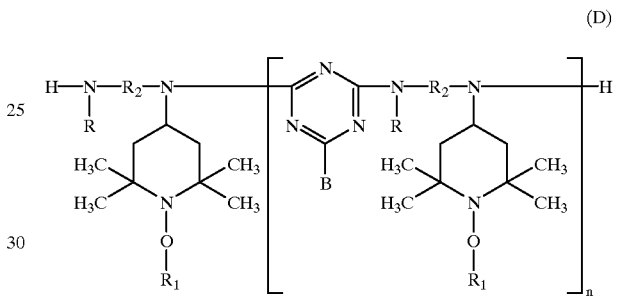
(D)

3) reacting the mixture obtained in 2) with a compound of the formula (E)

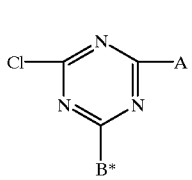
(E)

in a stoichiometric ratio to obtain a mixture as defined in claim 13; the radicals A, B, B*, R, $R_1$ and $R_2$ being as defined in claim 1 and the reactions 1) to 3) being carried out in an organic solvent in the presence of an inorganic base.

21. A method according to claim 20, wherein the molar ratio of the compound of the formula (C) to the compound of the formula (B) is 1:2 and n is 2, 4 and 6.

22. A mixture obtainable by a method according to claim 20.

23. A composition containing an organic material susceptible to degradation induced by light, heat or oxidation and at least one compound of the formula (I) according to claim 1.

24. A composition according to claim 23, wherein the totality of the compounds of the formula (I) being present in the composition has a polydispersity $\overline{M}w/\overline{M}n$ of 1 to 1.7.

25. A composition according to claim 23, wherein the organic material is a synthetic polymer.

26. A composition according to claim 23, wherein the organic material is polyethylene or polypropylene.

27. A method for stabilizing an organic material against degradation induced by light, heat or oxidation, which comprises incorporating into said organic material at least one compound of the formula (I) according to claim 1.

28. A compound of the formula (D)

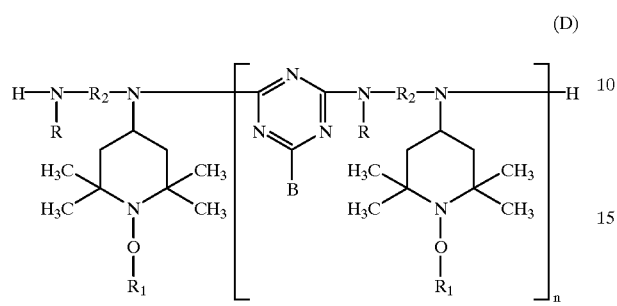

(D)

in which the polydispersity $\overline{Mw}/\overline{Mn}$ is 1;

n is 2, 3, 4, 5, 6, 7, 8, 9, 10, 11, 12, 13 or 14;

the radicals $R_1$ are independently of one another hydrogen, a hydrocarbyl radcal or —$OR_1$ is —O;

the radicals $R_2$ are independently of one another $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ being $C_1$–$C_{12}$acyl or ($C_1$–$C_{12}$alkoxy)carbonyl or having one of the definitions of $R_4$ given below except hydrogen;

or $R_2$ is a group of the formula (a), (b) or (c);

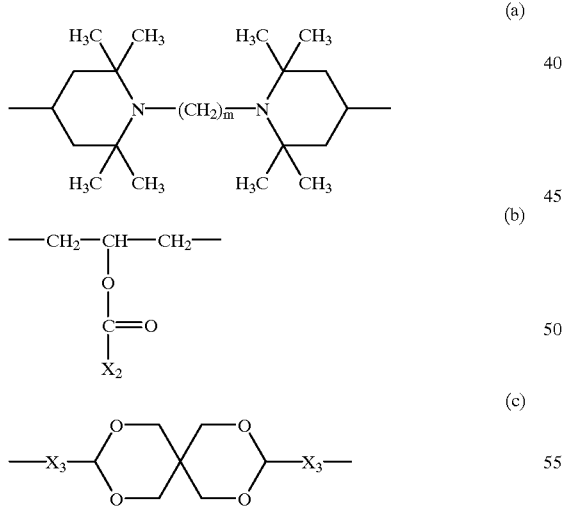

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

B is $OR_3$, —$N(R_4)(R_5)$ or a group of the formula (II);

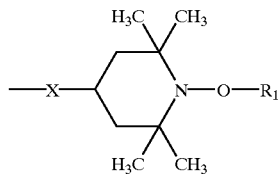

(II)

$R_3$, $R_4$ and $R_5$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

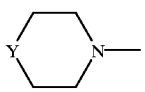

(III)

with Y being —O—, —$CH_2$—, —$CH_2CH_2$— or >N—$CH_3$, or —$N(R_4)(R_5)$ is additionally a group of the formula (III);

X is —O— or >N—$R_6$;

$R_6$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV),

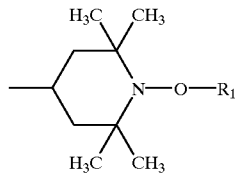

(IV)

or $C_2$–$C_4$alkyl which is substituted in the 2, 3 or 4 position by —OH, $C_1$–$C_8$alkoxy, di($C_1$–$C_4$alkyl)amino or a group of the formula (III); and the radicals R have independently of one another one of the meanings given for $R_6$;

with the proviso that in the individual recurrent units of the formula (D), each of the radicals B, R, $R_1$ and $R_2$ has the same or a different meaning.

29. A mixture containing at least three different compounds of the formula (D) according to claim 28, which vary only by the variable n, said mixture having a polydispersity $\overline{Mw}/\overline{Mn}$ of 1.1 to 1.7.

* * * * *